US012583868B2

(12) United States Patent
Ouvry et al.

(10) Patent No.: US 12,583,868 B2
(45) Date of Patent: Mar. 24, 2026

(54) JAK INHIBITORS AND METHODS FOR SYNTHESIZING AND USING THEREOF

(71) Applicant: GALDERMA HOLDING SA, Zug (CH)

(72) Inventors: Gilles Ouvry, Abingdon (GB); Branislav Musicki, Nice (FR); Craig Harris, Biot (FR); Etienne Thoreau, Grasse (FR)

(73) Assignee: Galderma Holding SA, Zug (CH)

( * ) Notice: Subject to any disclaimer, the term of this patent is extended or adjusted under 35 U.S.C. 154(b) by 454 days.

(21) Appl. No.: 18/120,767

(22) Filed: Mar. 13, 2023

(65) Prior Publication Data

US 2023/0212188 A1 Jul. 6, 2023

Related U.S. Application Data

(63) Continuation of application No. PCT/IB2021/058266, filed on Sep. 10, 2021.

(60) Provisional application No. 63/078,054, filed on Sep. 14, 2020.

(51) Int. Cl.

| | |
|---|---|
| ***C07D 498/14*** | (2006.01) |
| ***A61P 17/00*** | (2006.01) |
| ***A61P 29/00*** | (2006.01) |
| ***A61P 35/00*** | (2006.01) |
| *C07D 498/04* | (2006.01) |

(52) U.S. Cl.

CPC ............ *C07D 498/14* (2013.01); *A61P 17/00* (2018.01); *A61P 29/00* (2018.01); *A61P 35/00* (2018.01)

(58) Field of Classification Search

CPC .................................................... C07D 498/14

See application file for complete search history.

(56) References Cited

U.S. PATENT DOCUMENTS

| | | | |
|---|---|---|---|
| 2015/0376203 A1 | 12/2015 | Zhao et al. | |
| 2021/0061813 A1 | 3/2021 | Wishart et al. | |

FOREIGN PATENT DOCUMENTS

| | | |
|---|---|---|
| CN | 102292333 A | 12/2011 |
| CN | 102711476 A | 10/2012 |
| WO | WO-2011/068881 | 6/2011 |
| WO | WO-2020/088659 A1 | 5/2020 |

OTHER PUBLICATIONS

International Search Report and Written Opinion on PCT Appl. Ser. No. PCT/IB2021/058266 dated Dec. 2, 2021 (17 pages).

Namour et al.(2015) Pharmacokinetics and Pharmacokinetic/ Pharmacodynamic Modeling of Filgotinib (GLPG0634), a Selective JAK1 Inhibitor, in Support of Phase IIB Dose Selection), Clin Pharmacokinet, vol. 54, Feb. 14, 2015, pp. 859-874.

Pesu et al.(2008) "Therapeutic targeting of janus kinases", Immunological Reviews, vol. 223, Jun. 2008, pp. 132-142.

Schwartz et al. (2017) "JAK inhibition as a therapeutic strategy for immune and inflammatory diseases", Nature Reviews, Drug Discovery, vol. 17, No. 1, Dec. 2, 20178, pp. 1-41.

*Primary Examiner* — Susanna Moore

(74) *Attorney, Agent, or Firm* — Sunit Talapatra; Foley & Lardner LLP

(57) ABSTRACT

Novel compounds having formula (I) and methods of using these compounds to treat diseases, conditions, and disorders are described.

(I)

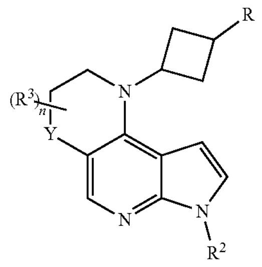

12 Claims, 6 Drawing Sheets

JAK INHIBITORS AND METHODS FOR SYNTHESIZING AND USING THEREOF

RELATED APPLICATIONS

This application is a continuation of PCT Patent Application No. PCT/IB2021/058266 filed Sep. 10, 2021, which application claims priority under 35 U.S.C. § 119(e) to U.S. Provisional Application No. 63/078,054 filed Sep. 14, 2020, the entire contents of all of which are incorporated herein by reference.

TECHNICAL FIELD

The present disclosure relates to novel compounds of formula (I) below:

(I)

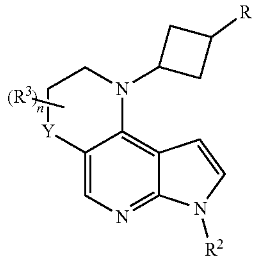

to the process for synthesizing the compounds of formula (I), and to the use of the compounds of formula (I) in pharmaceutical compositions for the treatment of diseases, conditions, and disorders. The compounds of the present disclosure act as inhibitors of Janus kinase (JAK), particularly JAK1. They are consequently of use in the treatment of JAK1 mediated diseases, conditions, or disorders.

BACKGROUND

Protein kinases (PKs) regulate diverse biological processes including tissue repair, cell growth, survival, organ formation, neovascularization, differentiation, morphogenesis, and regeneration, among others. Protein kinases also play specialized roles in a host of human diseases including cancer. Cytokines encompasses many structurally unrelated proteins that are grouped based on their binding to distinct receptor superfamilies. Cytokines influence cell differentiation, proliferation and activation, and can modulate both pro-inflammatory and anti-inflammatory responses to allow the host to react appropriately to pathogens. Type I and Type II cytokine receptors is a family of receptors which employ Janus Kinases (JAKs) for intracellular signaling [Schwartz, Daniella M et al. *Nature reviews. Drug discovery*, vol. 17, 1 (2017): 78]. The JAKs are intracellular cytoplasmic tyrosine kinases, which signal in pairs and transduce cytokine signaling from membrane receptors via the signal-transducer and activator of transcription (STAT) factors to the cell nucleus. The JAKs possess two near-identical phosphate-transferring domains. One domain exhibits the kinase activity, while the other negatively regulates the kinase activity of the first (pseudokinase).

Four different types of JAKs are known: JAK1, JAK2, JAK3 (also known as Janus kinase, leukocyte; JAKL; and L-JAK), and TYK2 (protein-tyrosine kinase 2). [Namour, F., et al., *Clin Pharmacokinet,* 54, 859-874 (2015)]. Each JAK has a primary role in mediating signaling by a subset of factors, although there may be some overlapping role for the different JAKs. For example, JAK1 is a novel target for inflammatory diseases, transducing cytokine-driven proinflammatory signaling, and for other diseases driven by JAK-mediated signal transduction. JAK2 signals for a range of cytokines, but is used primarily by receptors for hematopoietic growth factors, such as erythropoietin and thrombopoietin (TPO). JAK3 has been studied for its primary role in mediating immune function, whereas Tyk2 functions in association with JAK2 or JAK3 to transduce signaling of cytokines, such as interleukin-12 and -23 (IL-12 and IL-23) [Pesu, Marko et al., *Immunological reviews*, vol. 223 (2008): 132-42]. While JAK1, JAK2, and Tyk2 are expressed in many cell types and tissues, JAK-3 expression is skewed to hematopoietic and lymphoid precursor cells.

Inhibition of JAK1 has been associated with reductions in proinflammatory cytokines, such as interleukin-6 (IL-6) and interferons (IFN) α, β, and γ, and thereby with control of inflammation. JAK inhibitors such as Abrocitinib, Upadacitinib, Baricitinib, Tofacitinib, Ruxolitinib, Delgocitinib, Brepocitinib, Oclacitinib, Peficitinib and Fedratinib, are already known. However, a large number of these inhibitors do not act selectively on the JAK1 enzyme compared with other enzymes of the family. Selective inhibition of JAK1 may translate in to enhanced efficacy and reduced undesirable effects associated with inhibition of JAK2, JAK3, and Tyk2. For example, oral dosage forms of Upadacitinib and Baricitinib have been approved for treatment of Rheumatoid Arthritis with a black box warning regarding serious side effects such as thrombosis, malignancy (Lymphoma) and serious infections leading to hospitalization or death. While some of these oral drugs are being repositioned and repurposed for other forms of administration, the systemic undesired effects of these drugs is still an impediment to their successful development.

The JAK-STAT pathway has been found to play a fundamental role in human health and disease, from rare monogenic disorders to more common complex diseases. Agents that selectively inhibit or reduce JAK1 production and activity, while eliminating the systemic side effects, are of great interest as therapeutic targets for the treatment of various diseases involving expression of JAK1, including autoimmune, inflammatory and oncological diseases.

SUMMARY

The present disclosure provides novel compounds having formula (I)

(I)

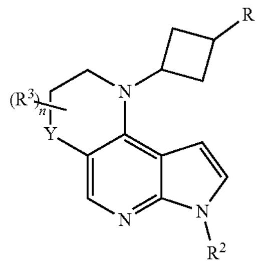

a salt thereof, or an enantiomer thereof, wherein:

Y is O, S, N or —CH;

R is a hydrogen atom, an alkyl radical, a substituted alkyl radical, an alkenyl radical, a substituted alkenyl radical, an alkynyl radical, a substituted alkynyl radical, $—OR^a$, $—NO_2$, $—C(O)R^b$, $—C(O)OR^a$, $—C(O)NR^cR^d$, $—SR^a$, $—S(O)R^b$, $—S(O)_2R^b$, $—S(O)NR^cR^d$, $—S(O)_2NR^cR^d$, $—NR^cR^d$, $—NR^cC(O)R^b$, $—NR^cC(O)NR^cR^d$, $—NR^cC(O)OR^a$, $—NR^cS(O)_2R^b$, $—NR^cS(O)_2NR^cR^d$, $—NR^cNR^cR^d$, $—NR^cNR^cC(O)R^b$, $—NR^cR^cC(O)NR^cR^d$, $—NR^cNR^cCC(O)OR^a$, $—CR^cR^dS(O)_2R^b$, $—CR^cR^dS(O)_2NR^cR^d$, $—OR^a$, $—OC(O)R^b$ or $—OC(O)NR^cR^d$;

$R^2$ is a hydrogen atom, an alkyl radical or a substituted alkyl radical, an alkenyl radical, a substituted alkenyl radical, an alkynyl radical, a substituted alkynyl radical, an aryl radical, a substituted aryl radical, a heterocyclic radical, or a substituted heterocyclic radical;

$R^3$ is independently selected from a hydrogen atom, an alkyl radical, a substituted alkyl radical, an alkenyl radical, a substituted alkenyl radical, an alkynyl radical, a substituted alkynyl radical, an alkoxy radical, a haloalkyl radical, a halogen, a cycloalkyl radical, a substituted cycloalkyl radical, —CN, $—NO_2$, $—C(O)OR^a$, $—C(O)NR^cR^d$, or $—NR^cR^d$;

each of $R^a$, $R^b$, $R^c$ and $R^d$ is independently selected from a hydrogen atom, an alkyl radical, a substituted alkyl radical, an alkenyl radical, a substituted alkenyl radical, an alkynyl radical, a substituted alkynyl radical, a haloalkyl radical, a cycloalkyl radical, a substituted cycloaklyl radical, a heterocyclic radical, a substituted heterocyclic radical, an aryl radical, a substituted aryl radical, a heteroaralkyl radical, or a substituted heteroaralkyl radical;

or $R^c$ and $R^d$ taken together with the nitrogen to which they are attached forms a heterocyclic radical, a substituted heterocyclic radical, a heteroaryl radical or a substituted heteroaryl radical; and n is 0, 1 or 2.

The present disclosure also provides salts and enantiomers, including pharmaceutically acceptable salts and enantiomers, of the compound of formula (I). The present disclosure also provides compositions and pharmaceutical compositions comprising the compound of formula (I) and a carrier or a pharmaceutically acceptable carrier.

The compounds disclosed herein are JAK inhibitors, specifically JAK1 inhibitors. Accordingly, the present disclosure provides pharmaceutical compositions comprising the compound of formula (I), a salt thereof, or an enantiomer thereof and methods of using the compound of formula (I), a salt thereof, or an enantiomer thereof for the treatment of diseases, disorders, or conditions associated with JAK1 release. The present disclosure also provides method of treating a disease, disorder, or condition involving JAK production and/or activity, wherein the method comprises administering to a subject, a pharmaceutical composition comprising the compound of formula (I) to inhibit the production and/or activity of JAK1 in the subject.

DETAILED DESCRIPTION

Figure 1:
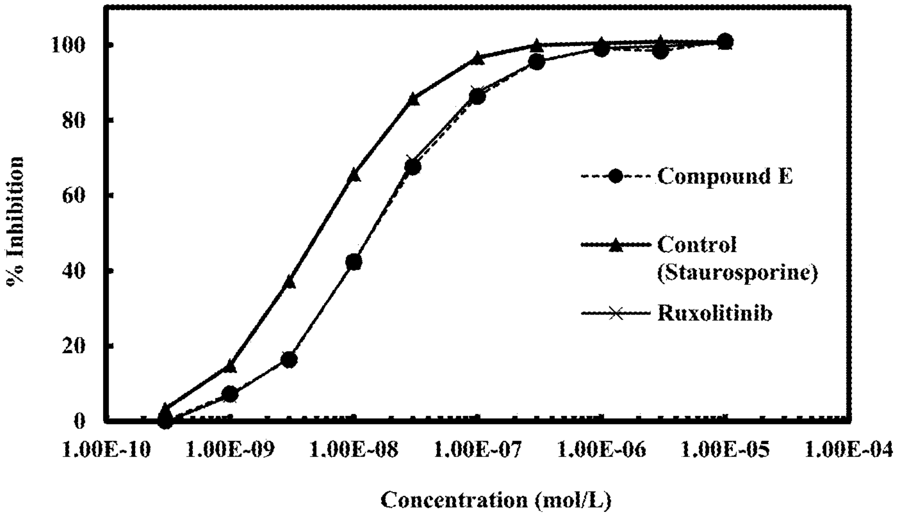
FIG. 1 illustrates concentration vs. % inhibition curve for JAK1 activity (1 mM) for the Staurosporine control sample, Compound E and Ruxolitinib.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

Unless the context indicates otherwise, it is specifically intended that the various features of the invention described herein can be used in any combination. Moreover, the disclosure also contemplates that in one or more embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

Definitions

As used herein, "about" will be understood by persons of ordinary skill in the art and will vary to some extent depending upon the context in which it is used. If there are uses of the term which are not clear to persons of ordinary skill in the art, given the context in which it is used, such as before a numerical designation, e.g., temperature, time, amount, and concentration, including range, indicates approximations which may vary by (+) or (−) 10%, 5% or 1%.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The expression "comprising" means "including, but not limited to." For example, compositions and methods include the recited elements, but do not exclude others. "Consisting essentially of" shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "alkyl radical" denotes a linear or branched, saturated hydrocarbon-based chain containing from 1 to 10 carbon atoms.

As used herein, the term "lower alkyl radical" denotes a linear or branched, saturated hydrocarbon-based chain containing from 1 to 5 carbon atoms.

As used herein, the term "alkenyl radical" denotes a linear or branched, unsaturated hydrocarbon-based chain containing from 2 to 10 carbon atoms and comprising one or more double bonds.

As used herein, the term "alkynyl radical" denotes a linear or branched, unsaturated hydrocarbon-based chain containing from 2 to 10 carbon atoms and comprising one or more triple bonds.

As used herein, the term "substituted alkyl radical" denotes a linear or branched, saturated hydrocarbon-based chain containing from 1 to 10 carbon atoms and substituted with one or more radicals or atoms, such as a halogen atom, an alkoxy radical, a cycloalkyl radical, a heterocyclyl radical, a heteroaryl radical or a hydroxyl radical.

As used herein, the term "substituted alkenyl radical" denotes a linear or branched, unsaturated hydrocarbon-based chain containing from 2 to 10 carbon atoms, comprising one or more double bonds and substituted with one or more radicals or atoms, such as a halogen atom, an alkoxy radical, a cycloalkyl radical, a heterocyclyl radical, a heteroaryl radical or a hydroxyl radical.

As used herein, the term "substituted alkynyl radical" denotes a linear or branched, unsaturated hydrocarbon-based chain containing from 2 to 10 carbon atoms, comprising one or more triple bonds and substituted with one or more radicals or atoms, such as a halogen atom, an alkoxy radical, a cycloalkyl radical, a heterocyclyl radical, a heteroaryl radical or a hydroxyl radical.

As used herein, the term "cycloalkyl radical" denotes a cyclic saturated hydrocarbon-based chain containing from 3 to 7 carbon atoms.

As used herein, the term "substituted cycloalkyl radical" denotes a cyclic saturated hydrocarbon-based chain containing from 3 to 7 carbon atoms and substituted with one or more radicals chosen from a halogen atom, an alkoxy radical, a heterocyclyl radical, a heteroaryl radical and a hydroxyl radical.

As used herein, the term "aryl radical" denotes an aromatic hydrocarbon-based ring or two fused aromatic hydrocarbon-based rings. Examples of aryl radicals include phenyl and naphthyl radicals.

As used herein, the term "substituted aryl radical" denotes an aromatic hydrocarbon-based ring or two or more fused aromatic hydrocarbon-based rings which is (are) substituted with one or more radicals or atoms, such as an alkyl, an alkoxy, an aryl, a heterocyclyl radical, a heteroaryl radical, a halogen, a hydroxyl, a cyano, a trifluoromethyl, or a nitro.

As used herein, the term "aralkyl radical" denotes an alkyl substituted with an aryl.

As used herein, the term "substituted aralkyl radical" denotes an aralkyl substituted with one or more radicals or atoms.

As used herein, the term "heterocyclic radical" denotes a saturated or unsaturated, cyclic or polycyclic hydrocarbon-based chain comprising one or more heteroatoms chosen from O, S, and N.

As used herein, the term "substituted heterocyclic radical" denotes a heterocyclic radical substituted with one or more radicals or atoms, such as an alkyl, an alkoxy, a cycloalkyl radical, a heteroaryl radical a halogen, a hydroxyl, a cyano, a trifluoromethyl, or a nitro.

As used herein, the term "heteroaryl radical" denotes an aromatic heterocyclic radical, i.e. a cyclic or polycyclic aromatic hydrocarbon-based chain, comprising one or more heteroatoms chosen from O, S, and N.

As used herein, the term "substituted heteroaryl radical" denotes a heteroaryl radical substituted with one or more radicals or atoms, such as an alkyl, an alkoxy, an aryl, a substituted aryl, a halogen, a hydroxyl, a cyano, a trifluoromethyl, or a nitro.

As used herein, the term "heteroaralkyl radical" denotes an alkyl radical substituted with a heteroaryl radical.

As used herein, the term "substituted heteroaralkyl radical" denotes a heteroaralkyl radical substituted with one or more radicals or atoms, such as an alkyl, an alkoxy, a halogen, a hydroxyl, a cyano, a trifluoromethyl, or a nitro.

As used herein, the term "alkoxy radical" denotes an oxygen atom substituted with an alkyl radical. The alkyl radical may be branched, linear, substituted, or unsubstituted.

As used herein, the term "halogen" or "halo" denotes a fluorine, chlorine, bromine, or iodine atom.

As used herein, the term "amine radical" may be a primary, secondary or tertiary amine radical. The amine radical may be branched, linear, substituted, or unsubstituted.

As used herein, the term "substituted amine radical" denotes an amine radical substituted with one or more radicals, e.g., a hydrocarbon group.

As used herein, the term "cyclic amine" denotes a radical in which the nitrogen has been incorporated into a ring structure. An example of a cyclic amine may be a cyclic alkyl amine.

As used herein, the term "heterocyclic amine" denotes a saturated or unsaturated cyclic amine comprising one or more heteroatoms, such as O, S, or N.

The terms "optional" or "optionally" as used throughout the specification means that the subsequently described event or circumstance may but need not occur, and that the description includes instances where the event or circumstance occurs and instances in which it does not.

The term "optionally substituted" refers to a substituted or unsubstituted group. The group may be substituted with one or more substituents, such as e.g., 1, 2, 3, 4 or 5 substituents.

In addition to the substituents defined herein, "substituted" refers to an alkyl, alkenyl, alkynyl, aryl, heteroaryl, heterocyclyl, ether or cycloalyl group, as defined herein (e.g., an alkyl group) in which one or more bonds to a hydrogen atom contained therein are replaced by a bond to non-H or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: alkyl, haloalkyl, halogen (i.e., F, Cl, Br, and I), hydroxyls, alkoxy, alkenoxy, alkynoxy, aryloxy, aralkyloxy, heterocyclyloxy, and heterocyclylalkoxy groups, carbonyls (oxo), carboxyls, esters, urethanes, oximes, hydroxylamines, alkoxyamines, aralkoxyamines, thiols, sulfides, sulfoxides, sulfones, sulfonyls, sulfonamides, amines, N-oxides, hydrazines, hydrazides, hydrazones, azides, amides, ureas, amidines, guanidines, enamines, imides, isocyanates, isothiocyanates, cyanates, thiocyanates, imines, nitro groups, nitriles (i.e., CN), and the like. All substituents can be further substituted.

As used herein, the term "stereoisomer" refers to both enantiomers and diastereomers.

As used herein, the term "derivatives" means both the metabolic derivatives thereof and the chemical derivatives thereof.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, the term treatment excludes prevention or prophylaxis.

As used herein, the term "subject" is used interchangeably with "patient," and indicates a mammal, or a human, ovine, bovine, feline, canine, equine, simian, etc. Non-human animals subject to diagnosis or treatment include, for example, simians, murine, such as, rat, mice, canine, leporid, livestock, sport animals, and pets. In one or more embodiments, the subject is a human.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response.

The term "pharmaceutically acceptable" as used herein refers to safe and sufficiently non-toxic for administration to a subject. By way of non-limiting example, some pharmaceutically acceptable salt or ester that are contemplated for use in connection with the present invention include those formed with an inorganic base, organic base, inorganic acid, organic acid, or amino acid (basic or acidic amino acid). Salts of inorganic bases can be, for example, salts of alkali metals such as sodium or potassium; alkaline earth metals such as calcium and magnesium or aluminum; and ammonia. Salts of organic bases can be, for example, salts trimethylamine, triethylamine, pyridine, picoline, ethanolamine, diethanolamine, and triethanolamine. Salts of inorganic acids can be, for example, salts of hydrochloric acid, hydroboric acid, nitric acid, sulfuric acid, and phosphoric acid. Salts of organic acids can be, for example, salts of formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides. Amino acid salts can be, for example, salts of glycine, alanine, arginine, asparagine, aspartic acid, cysteine, glutamine, glutamic acid, histidine, isoleucine, leucine, lysine, methionine, phenylalanine, serine, tryptophan, threonine, tyrosine, valine, citrulline, or ornithine.

The present disclosure provides novel compounds which are useful as an inhibitor of protein kinases, such as the enzyme Janus Kinase (JAK), specifically, Janus Kinase 1 (JAK1) enzyme. These novel compounds are therefore potential active ingredients for a variety of therapeutic the treatment of pathological conditions which involves inhibition or reduction of JAK1 production and/or activity.

Compounds

The JAK/STAT pathway is increasingly an attractive therapeutic target for a wide range of diseases owing to the wide range of effector molecules that use the pathway. JAK inhibitors target cytokine signaling by either oral or topical administration. The efficacy and safety profiles of known JAK inhibitors have not always corresponded with the selectivity of these drugs. In particular, the systemic treatments using the known JAK inhibitors have potential side effects, because of which many of the oral JAK inhibitors are being repurposed for topical use, which reduce the side effects. Despite these developments, there is still a need for more effective agents for the treatment of diseases. We have now discovered that a series of pyrrolo-pyridine compounds are potent JAK1 inhibitors and are thus useful in therapy of JAK1 mediated disorders.

Accordingly an object of the present disclosure is to provide novel JAK inhibitor compounds, particularly JAK1 inhibitor compounds for use in the treatment of a variety of potential indications in various dosage forms including topical, inhaled and nasal administration. In some aspects, the present disclosure provides a topical by design JAK1 inhibitor for the local treatment of immuno-inflammatory disorders. The compounds, compositions and methods of the present disclosure are advantageous compared to other topical JAK inhibitors in that they have higher efficacy vs topical standard of care, better safety through low systemic exposure and no systemic effect, and can be formulated for innovative dosing schedules and delivery methods. The novel compounds, compositions and methods of the present disclosure are designed to increase body surface area (BSA) with lower systemic exposure. The compounds and compositions of the present disclosure may exhibit large therapeutic indices, and are expected to provide a wide therapeutic window between the beneficial therapeutic effects and the onset of undesirable systemic side effects associated with JAK inhibition. The novel compounds, compositions and methods of the present disclosure are designed for (a) improved systemic safety profile through limited systemic exposure, (b) improved topical efficacy by way of enhanced skin penetration and increased JAK1 potency, and (c) better local tolerability and improved safety profile by way of higher plasmatic clearance and selectivity profile.

Novel compounds of formula (I) provided herein exhibit a good JAK1-inhibiting activity, and in particular inhibit the JAK1 enzyme selectively compared with other JAK family members. Thus, the present disclosure provides compounds of formula (I) below:

(I)

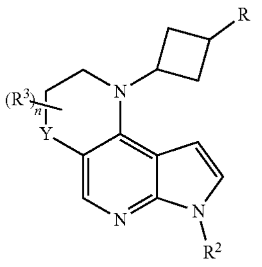

a salt thereof, or an enantiomer thereof;

wherein:

Y is O, S, N or —CH;

R is a hydrogen atom, an alkyl radical, a substituted alkyl radical, an alkenyl radical, a substituted alkenyl radical, an alkynyl radical, a substituted alkynyl radical, —$OR^a$, —$NO_2$, —$C(O)R^b$, —$C(O)OR^a$, —$C(O)NR^cR^d$, —$SR^a$, —$S(O)R^b$, —$S(O)_2R^b$, —$S(O)NR^cR^d$, —$S(O)_2NR^cR^d$, —$NR^cR^d$, —$NR^cC(O)R^b$, —$NR^cC(O)NR^cR^d$, —$NR^cC(O)OR^a$, —$NR^cS(O)_2R^b$, —$NR^cS(O)_2NR^cR^d$, —$NR^cNR^cR^d$, —$NR^cNR^cC(O)R^b$, —$NR^cNR^cC(O)NR^cR^d$, —$NR^cNR^cC(O)OR^a$, —$CR^cR^dS(O)_2R^b$, —$CR^cR^dS(O)_2NR^cR^d$, —$OR^a$, —$OC(O)R^b$ or —$OC(O)NR^cR^d$;

$R^2$ is a hydrogen atom, an alkyl radical or a substituted alkyl radical, an alkenyl radical, a substituted alkenyl radical, an alkynyl radical, a substituted alkynyl radical, an aryl radical, a substituted aryl radical, a heterocyclic radical, or a substituted heterocyclic radical;

$R^3$ is independently selected from a hydrogen atom, an alkyl radical, a substituted alkyl radical, an alkenyl radical, a substituted alkenyl radical, an alkynyl radical, a substituted alkynyl radical, an alkoxy radical, a haloalkyl radical, a halogen, a cycloalkyl radical, a substituted cycloalkyl radical, —CN, —$NO_2$, —$C(O)OR^a$, —$C(O)NR^cR^d$, or —$NR^cR^d$.

each of $R^a$, $R^b$, $R^c$ and $R^d$ is independently selected from a hydrogen atom, an alkyl radical, a substituted alkyl radical, an alkenyl radical, a substituted alkenyl radical, an alkynyl radical, a substituted alkynyl radical, a haloalkyl radical, a cycloalkyl radical, a substituted cycloalyl radical, a heterocyclic radical, a substituted heterocyclic radical, an aryl radical, a substituted aryl radical, a heteroaralkyl radical, or a substituted heteroaralkyl radical;

or $R^c$ and $R^d$ taken together with the nitrogen to which they are attached forms a heterocyclic radical, a substituted heterocyclic radical, a heteroaryl radical or a substituted heteroaryl radical; and n is 0, 1 or 2.

In certain embodiments, R may be a hydrogen atom, an alkyl radical, a substituted alkyl radical, an alkenyl radical, a substituted alkenyl radical, an alkynyl radical, a substituted alkynyl radical, —$OR^a$, —$NO_2$, —$C(O)R^b$, —$C(O)OR^a$, —$C(O)NR^cR^d$, —$SR^a$, —$S(O)R^b$, —$S(O)_2R^b$, —$S(O)NR^cR^d$, —$S(O)_2NR^cR^d$, —$NR^cR^d$, —$NR^cC(O)R^b$, —$NR^cC(O)NR^cR^d$, —$NR^cC(O)OR^a$, —$NR^cS(O)_2R^b$, —$NR^cS(O)_2NR^cR^d$, —$NR^cNR^cR^d$, —$NR^cNR^cC(O)R^b$, —$NR^cNR^cC(O)NR^cR^d$, —$NR^cNR^cC(O)OR^a$, —$CR^cR^dS(O)_2R^b$, —$CR^cR^dS(O)_2NR^cR^d$, —$OR^a$, —$OC(O)R^b$ or —$OC(O)NR^cR^d$. In certain embodiments, R may be selected from the group consisting of —$NR^cR^d$, —$NR^cC(O)R^b$, —$NR^cC(O)NR^cR^d$, —$NR^cC(O)OR^a$, —$NR^cS(O)_2R^b$, —$NR^cS(O)_2NR^cR^d$, —$NR^cNR^cR^d$, —$NR^cNR^cC(O)R^b$, —$NR^cNR^cC(O)NR^cR^d$, and —$NR^cNR^cC(O)OR^a$. In certain embodiments, R is —$NR^cS(O)_2R^b$ or —$NR^cS(O)_2NR^cR^d$. In certain embodiments, R is —$NR^cS(O)_2R^b$.

In some embodiments, the present disclosure provides compounds of formula (II) wherein:

(II)

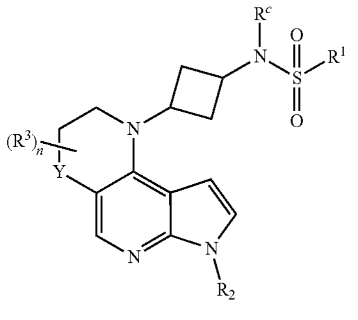

a salt thereof, or an enantiomer thereof, wherein:

Y is O, S, N or —CH;

$R^1$ is a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, an alkoxy radical, a substituted alkoxy radical, a cyclic amine radical, a heterocyclic radical, a substituted heterocyclic radical, a cycloalkyl radical, a substituted cycloaklyl radical, a heteroaralkyl radical, a substituted heteroaralkyl radical, a heterocyclic amine radical, —$NR^cR^d$, —$NR^cC(O)R^b$, —$NR^cC(O)OR^a$, —$NR^cC$ (O)$NR^cR^d$, —$NRS(O)R^b$, —$NR^cS(O)_2R^b$, —$NR^cS(O)_2NR^cR^d$, —$OC(O)R^b$, or —$OC(O)NR^cR^d$;

$R^2$ is a hydrogen atom, an alkyl radical or a substituted alkyl radical, an alkenyl radical, a substituted alkenyl radical, an alkynyl radical, a substituted alkynyl radical, an aryl radical, a substituted aryl radical, a heterocyclic radical, or a substituted heterocyclic radical;

$R^3$ is independently selected from a hydrogen atom, an alkyl radical, a substituted alkyl radical, an alkenyl radical, a substituted alkenyl radical, an alkynyl radical, a substituted alkynyl radical, an alkoxy radical, a haloalkyl radical, a halogen, a cycloalkyl radical, a substituted cycloalkyl radical, —CN, —$NO_2$, —C(O)$OR^a$, —C(O)$NR^cR^d$, or —$NR^cR^d$;

each of $R^a$, $R^b$, $R^c$ and $R^d$ is independently selected from a hydrogen atom, an alkyl radical, a substituted alkyl radical, an alkenyl radical, a substituted alkenyl radical, an alkynyl radical, a substituted alkynyl radical, a haloalkyl radical, a cycloalkyl radical, a substituted cycloaklyl radical, a heterocyclic radical, a substituted heterocyclic radical, an aryl radical, a substituted aryl radical, a heteroaralkyl radical, or a substituted heteroaralkyl radical;

or $R^c$ and $R^d$ taken together with the nitrogen to which they are attached forms a heterocyclic radical, a substituted heterocyclic radical, a heteroaryl radical or a substituted heteroaryl radical; and n is 0, 1, or 2.

In some embodiments, the present disclosure provides compounds of formula (II) wherein:

Y is O, S, N or —CH;

$R^1$ is a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, an alkoxy radical, a substituted alkoxy radical, a cyclic amine radical, a heterocyclic radical, a substituted heterocyclic radical, a cycloalkyl radical, a substituted cycloaklyl radical, a heteroaralkyl radical, a substituted heteroaralkyl radical, a heterocyclic amine radical;

$R^2$ is a hydrogen atom, a lower alkyl radical, or a lower alkyl radical substituted with a halogen atom;

$R^3$ is a hydrogen atom, a lower alkyl radical, a lower alkyl radical substituted with a halogen atom, a halogen atom, —CN, —$NO_2$, —C(O)$OR^a$, —C(O)$NR^cR^d$, —$S(O)_2R^b$, or —$NR^cR^d$;

each of $R^a$, $R^b$, $R^c$ and $R^d$ is independently selected from a hydrogen atom, an alkyl radical, a substituted alkyl radical, an alkenyl radical, a substituted alkenyl radical, an alkynyl radical, a substituted alkynyl radical, and a haloalkyl radical; or $R^c$ and $R^d$ taken together with the N in —$NR^cR^d$, form a heterocyclic radical and a substituted heterocyclic radical;

n is 0, 1, or 2.

In other embodiments, the present disclosure provides compounds of formula (II) wherein:

Y is O;

$R^1$ is a heterocyclic radical or a substituted heterocyclic radical, a cycloalkyl radical, a substituted cycloaklyl radical, a heteroaralkyl radical, a substituted heteroaralkyl radical, or a heterocyclic amine radical;

$R^2$ is a hydrogen atom, a lower alkyl radical or a lower alkyl radical substituted with a flourine atom;

$R^c$ is a hydrogen atom, an alkyl radical, a substituted alkyl radical; and n is 0.

In certain embodiments, $R^1$ may be a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, an alkoxy radical, a substituted alkoxy radical, a cyclic amine radical, a heterocyclic radical, a substituted heterocyclic radical, a cycloalkyl radical, a substituted cycloaklyl radical, a heteroaralkyl radical, a substituted heteroaralkyl radical, a heterocyclic amine radical, —$NR^cR^d$, —$NR^cC(O)R^b$, —$NR^cC(O)OR^a$, —$NR^cC(O)NR^cR^d$, —$NR^cS(O)R^b$, —$NR^cS(O)_2R^b$, —$NR^cS(O)_2NR^cR^d$, —$OC(O)R^b$, or —$OC(O)NR^cR^d$. In certain embodiments, $R^1$ may be a heterocyclic radical or a substituted heterocyclic radical, a cycloalkyl radical, a substituted cycloaklyl radical, a heteroaralkyl radical, a substituted heteroaralkyl radical, or a heterocyclic amine radical. In certain embodiments, $R^1$ may be a heterocyclic radical or a substituted heterocyclic radical. In certain embodiments, $R^1$ is a heterocyclic radical substituted with one more of a cycloalkyl radical or a substituted cycloalkyl radical. In certain embodiments, $R^1$ is a heterocyclic radical substituted with one more of a cycloalkyl radical or a substituted cycloalkyl radical. In certain embodiments, $R^1$ is a substituted heterocyclic radical wherein the heteroatom is substituted with one or more cycloalkyl radicals. In certain embodiments, $R^1$ is a substituted heterocyclic radical, wherein the heteroatom is substituted with a cycloalkyl radical. In certain embodiments, $R^1$ is an azetidinyl radical substituted with a cyclopropyl radical. In certain embodiments, $R^1$ is a 1-cycloproylazetidinyl radical.

In certain embodiments, $R^2$ may be a hydrogen atom, a lower alkyl radical or a lower alkyl radical substituted with a flourine atom. In certain embodiments, $R^2$ may be a $C_1$-$C_5$ alkyl radical or a $C_1$-$C_5$ alkyl radical substituted with a flourine atom. In certain embodiments, $R^2$ is a hydrogen atom, a methyl radical, an ethyl radical or —$CF_3$. In certain embodiments, $R^2$ is a hydrogen atom.

In certain embodiments, $R^3$ may be a hydrogen atom, a lower alkyl radical, a lower alkyl radical substituted with a halogen atom, a halogen atom, —CN, —$NO_2$, —C(O)$OR^a$, —C(O)$NR^cR^d$, —$S(O)_2R^b$, or —$NR^cR^d$. In certain embodiments, $R^3$ is a hydrogen atom.

In certain embodiments, n is 0, 1, or 2. In certain embodiments, n is 0 or 1. In certain embodiments, n is 0.

In certain embodiments, Y is O, S, N or —CH. In certain embodiments, Y is O, S or —CH. In certain embodiments, Y is O, N or —CH. In certain embodiments, Y is O, S, or N. In certain embodiments, Y is O or S. In certain embodiments, Y is O or N. In certain embodiments, Y is O or —CH. In certain embodiments, Y is O.

In certain embodiments, $R^2$ may be a hydrogen atom. In such a case, in certain embodiments, $R^1$ may be a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, an alkoxy radical, a substituted alkoxy radical, a cyclic amine radical, a heterocyclic radical, a substituted heterocyclic radical, a cycloalkyl radical, a substituted cycloaklyl radical, a heteroaralkyl radical, a substituted heteroaralkyl radical, a heterocyclic amine radical, —$NR^cR^d$, —$NR^cC(O)R^b$, —$NR^cC(O)OR^a$, —$NR^cC(O)NR^cR^d$, —$NR^cS(O)R^b$, —$NR^cS(O)_2R^b$, —$NR^cS(O)_2NR^cR^d$, —$OC(O)R^b$, or —$OC(O)NR^cR^d$. In certain embodiments, $R^1$ may be a heterocyclic radical or a substituted heterocyclic radical, a cycloalkyl radical, a substituted cycloaklyl radical, a heteroaralkyl radical, a substituted heteroaralkyl radical, or a heterocyclic amine radical. In certain embodiments, $R^1$ may be a heterocyclic radical or a substituted heterocyclic radical. In certain embodiments, $R^1$ is a heterocyclic radical substituted with one more of a cycloalkyl radical or a substituted cycloalkyl radical. In certain embodiments, $R^1$ is a heterocyclic radical substituted with one more of a cycloalkyl radical or a substituted cycloalkyl radical.

In certain embodiments, when n is 0, $R^2$ may be a hydrogen atom. In such a case, $R^1$ is a heterocyclic radical or a substituted heterocyclic radical.

In another aspect, the present disclosure provides compounds of formula (IIa) below:

(IIa)

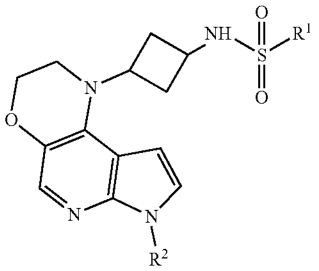

a salt thereof, or an enantiomer thereof,
wherein $R^1$ and $R^2$ are as defined for compound of formula (II).

In another aspect, the present disclosure provides compounds of formula (IIb) below:

(IIb)

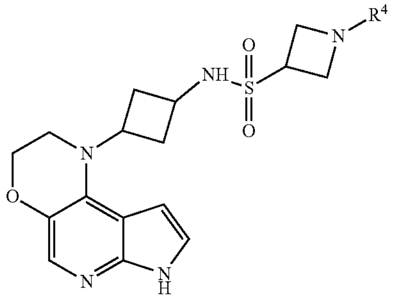

a salt thereof, or an enantiomer thereof,
wherein $R^1$, $R^3$ and n are as defined for compound of formula (II).

In certain embodiments, the compound of formula (I) is Compound E below:

(E)

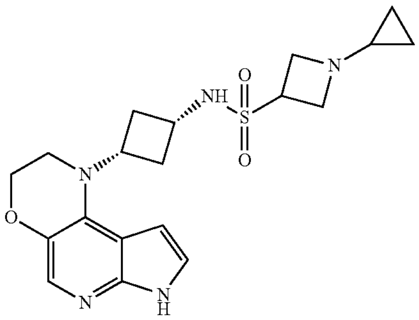

a salt thereof, or an enantiomer thereof.

In some embodiments, the present disclosure provides salts of the compound of formula (I), formula (II), formula (IIa) or formula (IIb). Moreover, the salts are pharmaceutically and/or physiologically acceptable salts of the compound of formula (I), formula (II), formula (IIa) or formula (IIb). Moreover, the present disclosure provides enantiomers, in particular pharmaceutically acceptable enantiomers, of the compound of formula (I), formula (II), formula (IIa) or formula (IIb).

The present disclosure not only provides the compound of formula (I), formula (II), formula (IIa) or formula (IIb) per se, but also its pharmaceutically acceptable salts, solvates, hydrates, esters, amides, stereoisomers, derivatives, polymorphs and prodrugs thereof, and also its various crystalline and amorphous forms. The pharmaceutically acceptable salts may include salts of the compounds of formula (I), formula (II), formula (IIa) or formula (IIb) formed with a pharmaceutically acceptable acid and salts of the compounds of formula (I), formula (II), formula (IIa) or formula (IIb) formed with a pharmaceutically acceptable base, such as identified above.

Compositions

Provided herein are pharmaceutical compositions comprising, consisting of, or consisting essentially of compound of formula (I), formula (II), formula (IIa) or formula (IIb) or an equivalent thereof. In any embodiments, the present disclosure provides a pharmaceutical composition comprising one or more of the compound of formula (I), formula (II), formula (IIa) or formula (IIb) as described herein, and a pharmaceutically acceptable carrier and/or excipient. In any embodiments, the pharmaceutical composition comprises a therapeutically effective amount of the compound of formula (I), formula (II), formula (IIa) or formula (IIb) and a pharmaceutically acceptable carrier or excipient. Suitable pharmaceutical carriers and excipients include those which are pharmaceutically acceptable and compatible with the selected method of administration. The pharmaceutical compositions described herein may contain various carriers or excipients known to those skilled in the art.

Suitable pharmaceutically acceptable excipients and carriers are generally known to those skilled in the art and are thus included in the present disclosure. Pharmaceutical compositions of compound of formula (I) or an equivalent thereof of the present disclosure can be prepared as formulations according to standard methods and using excipients and carriers which are described in Remington's Pharmaceutical Science, Mark Publishing Co., New Jersey (1991), which is incorporated herein by reference. Exemplary carriers or excipients may include, but are not limited to, emollients, ointment base, emulsifying agents, solubilizing agents, humectants, thickening or gelling agents, wetting agents, texture enhancers, stabilizers, pH regulators, osmotic pressure modifiers, emulsifiers, UV-A and UV-B screening agents, preservatives, permeation enhancer, chelating agents, antioxidants, acidifying agents, alkalizing agents, buffering agents and vehicle or solvent.

The pharmaceutical compositions may be administered in either single or multiple doses by any of the accepted modes of administration of agents having similar utilities, including for example orally, topically, intravenously, rectal, buccal, intranasal and transdermal routes, by intra-arterial injection, intraperitoneally, parenterally, subcutaneously, intramuscularly, as an inhalant or via an impregnated or coated device such as a stent. Pharmaceutical compositions of the present disclosure are preferably administered topically. Specifically, the pharmaceutical compositions are administered to subjects or patients by topical application. While the compositions may not be primarily designed for oral, ophthalmic, or intravaginal use, other administration methods are contemplated.

The pharmaceutical compositions of any embodiment herein may be formulated for topical administration or any of the routes discussed herein. In one or more embodiments, pharmaceutical compositions of compound of formula (I), formula (II), formula (IIa) or formula (IIb) or an equivalent thereof may be formulated as a composition for topical administration. The pharmaceutical compositions of the present disclosure are particularly suited for topical treatment of the skin and the mucous membranes, and may be in the form of ointments, creams, milks, pomades, powders, impregnated pads, solutions, gels, gel-creams, sprays, lotions, foams or suspensions. In one or more embodiments, the compositions may be in the form of suspensions of microspheres or nanospheres or of lipid or polymeric vesicles, or of polymeric patches and hydrogels for controlled release. These compositions for topical application may be in anhydrous form, in aqueous form or in the form of an emulsion. In one or more embodiments, the pharmaceutical composition of the present disclosure is in the form of a cream, a gel, a gel-cream or a lotion.

The present disclosure provides compositions, in particular pharmaceutical and cosmetic compositions, comprising one or more compounds of formula (I), formula (II formula (IIa) or formula (IIb) for the treatment of JAK1 mediated diseases, condition, or disorders. The present disclosure provides for the use of at least one compound of formula (I), formula (II), formula (IIa) or formula (IIb) for preparing a pharmaceutical or cosmetic composition in which the compound has JAK1 enzyme-inhibiting activity.

Methods of Treatment

Studies have shown the importance of JAKs and STAT in the homeostasis of the immune system which provides the rationale for targeting JAK-STAT signaling to treat autoimmune and inflammatory diseases. JAK1 is a human tyrosine kinase protein essential for signaling for certain type I and type II cytokines. It interacts with the common gamma chain (γc) of type I cytokine receptors, to elicit signals from the IL-2 receptor family (e.g. IL-2R, IL-7R, IL-9R and IL-15R), the IL-4 receptor family (e.g. IL-4R and IL-13R), the gp130 receptor family (e.g. IL-6R, IL-11R, LIF-R, OSM-R, cardiotrophin-1 receptor (CT-1R), ciliary neurotrophic factor receptor (CNTF-R), neurotrophin-1 receptor (NNT-1R) and Leptin-R). It is also important for transducing a signal by type I (IFN-α/β) and type II (IFN-γ) interferons, and members of the IL-10 family via type II cytokine receptors. JAK1 plays a critical role in initiating responses to multiple major cytokine receptor families, underlying the pathogenesis of allergic, inflammatory and autoimmune disorders. In particular, JAK1 plays a major role in the signaling of a number of proinflammatory cytokines which are known to play a role in many pathological conditions with an inflammatory nature.

Accordingly, in one aspect, provided are methods for treating diseases caused by and/or associated with deregulated protein kinase activity, particularly JAK activity, and further more particularly JAK1 activity, which comprises administering to a subject in need thereof an effective amount of a substituted pyrrolo-pyridine compounds represented by formula (I), formula (II), formula (IIa) or formula (IIb) as defined above.

In another aspect, the present disclosure provides the use of at least one compound of formula (I), formula (II), formula (IIa) or formula (IIb) as defined above, for the treatment of pathological diseases, conditions, and disorders linked to JAK1 release. A JAK1 inhibitor of formula (I), formula (II), formula (IIa) or formula (IIb) decreases JAK1 production. As a result, a JAK1 inhibitor is useful for the treatment of pathological conditions, disease, or disorders associated with JAK1 release.

In one aspect, the present disclosure provides for the use of one or more compounds of formula (I), formula (II), formula (IIa) or formula (IIb) as defined above, for the treatment of pathological diseases, conditions, or disorders which are improved by inhibiting the JAK1 enzyme. The one or more compounds may be in a pharmaceutical or cosmetic composition formulated for the treatment of JAK1 mediated diseases, disorders, or conditions.

The present disclosure provides a method of therapeutic (human or animal) or cosmetic treatment, which comprises administration or the application of a pharmaceutical or cosmetic composition comprising a compound of formula (I), formula (II), formula (IIa) or formula (IIb) as a JAK1 inhibitor and, consequently, as an inhibitor of JAK1 production. The method provided herein can be used to treat mammals, in particular humans.

The present disclosure provides a method of using one or more compounds of formula (I), formula (II), formula (IIa) or formula (IIb) as defined above, for the treatment of pathological diseases, conditions, or disorders linked to JAK1 production.

In another aspect, the present disclosure also relates to a method of using a compound of formula (I), formula (II), formula (IIa) or formula (IIb) as defined above, for preparing a medicament intended for the treatment of pathological diseases, conditions, or disorders for which reducing JAK1 production and/or activity is desired.

The compounds disclosed herein are particularly suitable for the treatment and prevention of diseases, disorders, or conditions, for which reducing JAK1 production and/or activity would be of great interest. These pathological conditions listed hereinafter in a nonlimiting manner are, for example, Rheumatoid Arthritis (RA), Atopic Dermatitis (AD), Alopecia Areata, Vitiligo, Chronic hand eczema, Psoriatic Arthritis, Ulcerative Colitis, Myelofibrosis, Polycythemia vera, Graft-versus-Host Disease (GVHD), Psoriasis, Sarcoidosis, Scleroderma, Morphea (localized scleroderma)/Eosinophilic fascitis, Crohn's disease, Asthma, Systemic lupus erythematosus (SLE), (Chronic) Cutaneous lupus erythematosus, Ilic fasciitis, Granuloma annulare, Mycosis Fungoides, Atopic asthma, COVID infection, Chronic itch, Dermatomyositis, Psoriasis Vulgaris, Hidradenitis Suppurativa, Lichen Planus, Inflammatory Bowel Disease, Single gene disorders, Eye diseases, and Cancer.

The present disclosure provides a method of using a compound of formula (I), formula (II), formula (IIa) or formula (IIb) as defined above, for preparing a medicament intended for the treatment of pathological conditions with an inflammatory nature, in which JAK1 is involved. The present disclosure provides a method of using a compound of formula (I), formula (II), formula (IIa) or formula (IIb) as defined above, for preparing a medicament intended for the treatment of autoimmune and/or inflammatory skin disorders, e.g., atopic dermatitis, vitiligo, chronic hand eczema and alopecia aerata. The present disclosure also provides a method of using a compound of formula (I), formula (II), formula (IIa) or formula (IIb) as defined above, for preparing a medicament intended for the treatment of atopic dermatitis.

The present disclosure also provides a method of using a compound of formula (I), formula (II), formula (IIa) or formula (IIb) as defined above, for preparing a medicament intended for the treatment of atopic dermatitis. The JAK1 inhibitor compounds described herein may mediate signaling from the major cytokines involved in the pathophysiology of atopic dermatitis, such as for e.g., IL-4, IL-5, IL-13, IL-31, and IL-22.

The present disclosure also provides a method of using a compound of formula (I), formula (II), formula (IIa) or formula (IIb) as defined above, for preparing a medicament intended for the treatment of chronic hand eczema, a skin condition with various etiologies involving JAK-dependent cytokines.

The present disclosure also provides a method of using a compound of formula (I), formula (II), formula (IIa) or formula (IIb) as defined above, for preparing a medicament intended for the treatment of alopecia aerata. Overexpression of JAK1/2/3 has been observed in skin of patients with alopecia aerate. Cytotoxic NKG2D-expressing CD8+ T cells have been shown to be central in alopecia aerata, causing up-regulation of IL-15 in hair follicles and ultimately production of IFN-g, which targets the hair follicle for attack. IFNg primarily signals through JAK1/2 and IL15 mostly through JAK1/3. JAK inhibitors (oral and topical) have been shown to eliminate the IFN signature and reverse disease in several animal models of alopecia aerate.

The present disclosure also provides a method of using a compound of formula (I), formula (II), formula (IIa) or formula (IIb) as defined above, for preparing a medicament intended for the treatment of Vitiligo. The pathogenesis of vitiligo involves the destruction of melanocytes via cell-mediated immunity, and studies show that IFN-γ and CD8+ T cells play a key role in this process. In particular, there is a strong IFN-γ-specific TH1 cytokine signature in lesional skin, with upregulation of associated cytokines CXCL9 and CXCL10. The JAK1 inhibitor compounds described herein may mediate IFNg signaling.

An effective amount of compound of formula (I), formula (II), formula (IIa) or formula (IIb) can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. The dosage can be determined by a physician and adjusted, as necessary, to suit observed effects of the treatment.

In one or more embodiments, a compound of formula (I), formula (II), formula (IIa) or formula (IIb) is administered thrice daily, twice daily, once daily, every other day, twice per week, three times per week, four times per week, five times per week, six times per week, once per week, once every two weeks, once every three weeks, once every four weeks, once every five weeks, once every six weeks, once every seven weeks, once every eight weeks, once every nine weeks, once every 10 weeks, once every 11 weeks, once every 12 weeks, twice per year, once per year, or any range including and/or in-between any two of these values, and/or as needed.

The treatments have a variable duration, depending on the patient and the therapy. The treatment period may thus run from several days to several years. In one or more embodiments, the duration of treatment is about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about one week, about 2 weeks, about 3 weeks, about 4 weeks, about 5 weeks, about 10 weeks, about 20 weeks, about 30 weeks, about 36 weeks, about 40 weeks, about 48 weeks, about 50 weeks, about one year, about two years, about three years, about four years, about five years, or any range including and/or in-between any two of these values, and/or as needed.

The present disclosure provides compounds exhibiting good JAK1-inhibiting activity and, in particular, they inhibit the JAK1 enzyme selectively compared with other JAKs. This JAK1 enzyme-inhibiting activity is measured in an enzymatic assay and quantified via the measurement of an $IC_{50}$ (inhibitory concentration necessary to obtain 50% inhibition of the JAK1 enzyme). The compounds provided herein have an $IC_{50}$ for JAK1 of less than or equal to 10 μM and more particularly less than or equal to 1 μM. Advantageously, the compounds described herein have an $IC_{50}$ for JAK1 less than or equal to 0.5 μM. Advantageously, these compounds are selective for JAK1 compared with the other JAKs: their inhibitory activity is at least 10 times greater for JAK1 than for other JAKs (i.e. the $IC_{50}$ value for JAK1 is at least 10 times smaller than that for other JAKs), and more advantageously at least 100 times greater.

Methods of Preparation

The present technology also encompasses the preparation of pharmaceutically acceptable salts, solvates, hydrates, esters, amides, stereoisomers, derivatives, polymorphs, prodrugs, and crystalline or amorphous forms of the compounds disclosed herein. Any or all of the compounds set forth in any of the reaction schemes herein may be converted to a pharmaceutically acceptable salt by reaction with an inorganic or organic acid or inorganic or organic base under appropriate conditions known to one skilled in the art. Pharmaceutically acceptable esters and amides can be prepared by reacting, respectively, a hydroxy or amino functional group with a pharmaceutically acceptable organic acid, such as identified above. A prodrug is a drug which has been chemically modified and may be biologically inactive at its site of action, but which is degraded or modified by one or more enzymatic or other in vivo processes to the parent bioactive form. Generally, a prodrug has a different pharmacokinetic profile than the parent drug such that, for example, it is more easily absorbed, it has better salt formation or solubility and/or it has better systemic stability.

The JAK1 inhibitor compounds described herein can be prepared by methods well known in the art of organic chemistry. The starting material used for the synthesis of these compounds can be either synthesized or obtained from commercial sources such but not limited Sigma-Aldrich Company. The compounds described and other related compounds having different substituents are optionally synthesized using techniques and such as for example, in *Fieser & Fieser's Reagents for Organic Synthesis*, Volumes 1-17 (John Wiley and Sons, 1991); *Organic Reactions*, Volumes 1-40 (John Wiley and Sons, 1991), *Larock's Comprehensive Organic Transformations* (VCH Publishers Inc., 1989), March, *Advanced Organic Chemistry* $4^{th}$ Ed., (Wiley 1992);

Carey & Sundberg, *Advanced Organic Chemistry* 4th Ed., Vols. A and B (Plenum 2000, 2001), and Green & Wuts, *Protective Groups in Organic Synthesis* 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein. The synthetic procedures described herein, especially when taken with the general knowledge in the art, provide sufficient guidance to those of ordinary skill in the art to perform the synthesis, isolation, and purification of the compounds of the present invention. Further, it is contemplated that the individual features of these embodiments and examples may be combined with the features of one or more other embodiments or examples.

It will also be appreciated by those skilled in the art that in the processes described below the functional groups of intermediate compounds may need to be protected by suitable protecting groups. Protecting groups may be added or removed in accordance with standard techniques, which are known to one of ordinary skill in the art and as described herein. The use of protecting groups is described in detail in Green, T. W. and P. G. M. Wuts, *Protective Groups in Organic Synthesis* (1999), 3rd Ed., Wiley.

In addition, at any point in any of the reaction schemes disclosed herein, the starting material, an intermediate or a product so formed may be subjected to a resolution process whereby individual enantiomers or diastereomers are separated into starting materials, intermediates or products that are in stereoisomerically substantially pure form. These individual enantiomers, diastereomers or mixtures thereof, can then be used in the method disclosed in any of the reaction schemes herein to prepare stereoisomerically substantially pure forms of the compounds of formula (I), formula (II), formula (IIa) or formula (IIb), or equivalent thereof or mixtures thereof. Methods for resolution of racemates or other stereoisomeric mixtures are well known in the art (e.g., E. L. Eliel and S. H. Wilen, in *Stereochemistry of Organic Compounds*; John Wiley & Sons: New York, 1994; Chapter 7, and references cited therein).

The following examples illustrate illustrative methods for illustrative compounds provided herein. These examples are not intended, nor are they to be construed, as limiting the scope of the disclosure. It will be clear that the methods can be practiced otherwise than as particularly described herein and for other compounds within the scope of the genus described herein. Numerous modifications and variations are possible in view of the teachings herein and, therefore, are within the scope of the disclosure.

EXAMPLES

Various embodiments will be further clarified by the following examples, which are in no way intended to limit this disclosure thereto.

General Abbreviations

AcOH Acetic acid
ATP Adenosine-5'-triphosphate
CbzCl Benzyl chloroformate
DCM Dichloromethane
DMF Dimethylformamide
DMSO Dimethylsulfoxide
DIPEA Diisopropylethylamine
DSC Differential scanning calorimetry
DTAD di-tert-butyl azodicarboxylate
DTT Dithiothreitol
EGTA Ethylene glycol-bis(β-aminoethyl ether)-N,N,N',N'-tetraacetic acid
EtOAc Ethyl acetate
HATU 2-(1H-7-Azabenzotriazol-1-yl)-1,1,3,3-tetramethyluronium-hexafluoro-phosphate
HPLC High Performance Liquid Chromatography
IPA Isopropyl alcohol
$IC_{50}$ Inhibitory concentration at which there is a 50% effect
JAK Janus kinase
MeCN Acetonitrile
MeOH Methanol
MsCl Methanesulfonyl chloride
MS Mass Spectroscopy
MTBE Methyl tert-butyl ether
NADPH Nicotinamide adenine dinucleotide phosphate
NCS N-Chlorosuccinimide
NMP N-Methyl-2-pyrrolidone
NMR Nuclear magnetic resonance
PBS Phosphate-buffered saline
PD pharmacodynamic
PK Pharmacokinetic
r.t. Room temperature
STAT signal transducer and activator of transcription protein
TEA Triethylamine
THF Tetrahydrofuran
TLC Thin Layer Chromatography
TYK Tyrosine kinase General Methods for the Preparation of the Compounds Representative compounds of formula (I) were synthesized and characterized as described below.

Example 1: Preparation of Compound E (CD14896)

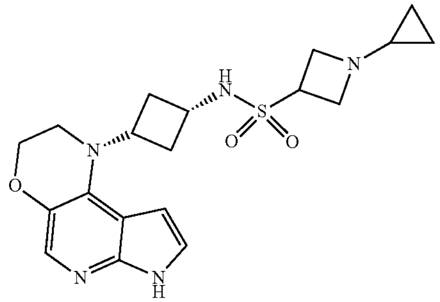

Compound E was synthesized according to the following scheme:

Scheme 1

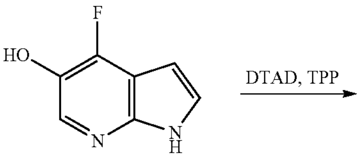

1

-continued

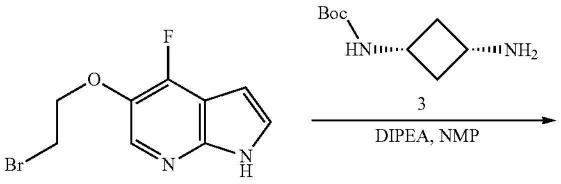

2

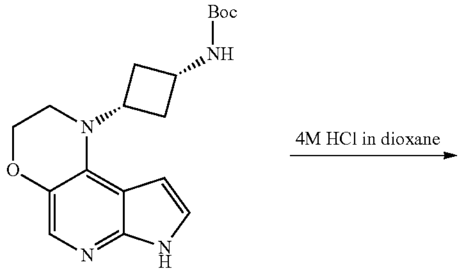

4

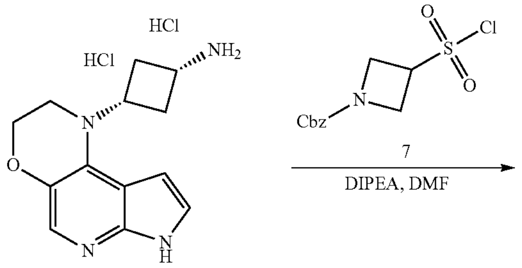

5

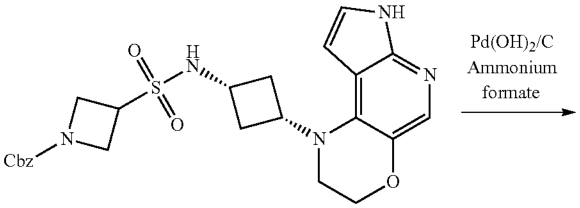

6

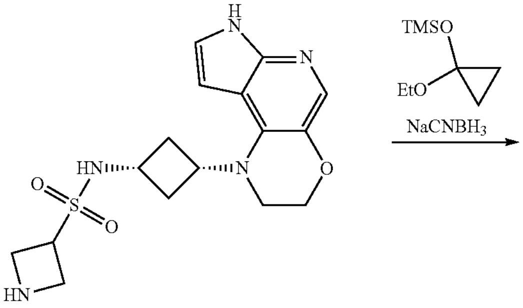

8

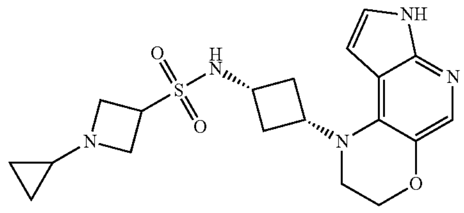

Compound E

Step A: 5-(2-Bromoethoxy)-4-fluoro-1H-pyrrolo[2,3-b]pyridine (2)

To a stirred solution of triphenylphosphine (19.4 g, 73.95 mmol) in THF (175 mL) at 0° C. was added DTAD (17.0 g, 73.95 mmol) and the mixture was stirred at 0° C. for 1.5 h. A precipitate of the resulting betaine formed and a suspension of 4-fluoro-1H-pyrrolo[2,3-b]pyridin-5-ol (9.0 g, 59.16 mmol) and 2-bromoethanol (9.24 g, 73.95 mmol) in THF (90 mL) was then added dropwise at 0° C. and the mixture was stirred at r.t. overnight. The mixture was concentrated under reduced pressure and taken up in MTBE (150 mL). Triphenylphosphine oxide precipitated and was removed by filtration and the filtrate was evaporated to afford an orange solid. The crude material was purified by silica gel column chromatography eluting with a gradient of 0-30% of EtOAc in cyclohexane to afford the title compound (12.7 g, 83%) as a white solid.

1H NMR ($CDCl_3$) δ 9.75 (s, 1H), 8.27 (d, 1H), 7.34 (s, 1H), 6.62 (s, 1H), 4.44 (t, J=6.5 Hz, 2H), 3.66 (t, J=6.5 Hz, 2H). MS (ESI): m/z=259, 261 [M+H]+

Step B: tert-Butyl ((cis)-3-(2,3-dihydropyrrolo[3',2':5,6]pyrido[3, 4-b][1,4]oxazin-1(7H)-yl)cyclobutyl) carbamate (4)

To a stirred solution of 5-(2-bromoethoxy)-4-fluoro-1H-pyrrolo[2,3-b]pyridine (3.89 g, 15.01 mmol) in NMP (35 mL) was added tert-butyl ((cis)-3-aminocyclobutyl)carbamate (3) (4.19 g, 22.52 mmol) and DIPEA (5.23 mL, 30.03 mmol) and the reaction mixture was stirred at 60° C. for 22 h. The reaction was allowed to cool down to r.t., was diluted with EtOAc (200 mL) and washed with water (2×100 mL) and brine (2×80 mL). The organic layer was dried over $Na_2SO_4$, filtered and concentrated under reduced pressure to afford the crude product as an orange oil. The crude material was purified by silica gel column chromatography eluting with a gradient of MeOH in DCM (0-5%) to afford the title compound (4) as a cream solid (3.39 g, 66%).

1H NMR ($CDCl_3$) δ 10.56 (s, 1H), 7.78 (s, 1H), 7.13 (d, J=3.7 Hz, 1H), 6.48 (d, J=3.7 Hz, 1H), 4.82 (s, 1H), 4.67 (tt, J=9.8, 7.2 Hz, 1H), 4.20-4.13 (m, 2H), 3.86 (s, 1H), 3.56 (t, J=4.5 Hz, 2H), 2.69 (tdt, J=9.8, 7.2, 2.7 Hz, 2H), 2.23 (d, J=10.5 Hz, 2H), 1.45 (s, 9H). MS (ESI): m/z=345 [M+H]+

Step C. (cis)-3-(2,3-Dihydropyrrolo[3',2':5,6]pyrido[3, 4-b][1,4]oxazin-1(7H)-yl)cyclobutan-1-amine dihydrochloride (5)

To a stirred solution of tert-butyl ((cis)-3-(2,3-dihydropyrrolo[3',2':5,6]pyrido [3,4-b][1,4]oxazin-1(7H)-yl)cyclobutyl)carbamate (3.39 g, 9.84 mmol) in dioxane (40 mL) was added HCl 4 M in dioxane (49 mL, 197 mmol). The reaction mixture was stirred at r.t. for 3 h. The solvent was concentrated to dryness under vacuum to afford the title compound (3.10 g, 99%) as a white solid.

1H NMR (DMSO-d6) δ 14.09 (s, 1H), 12.30 (s, 1H), 8.59-8.54 (br s, 3H), 7.86 (s, 1H), 7.37 (d, J=3.7 Hz, 2H), 6.96 (d, J=3.7 Hz, 2H), 4.89 (p, J=8.4 Hz, 1H), 4.22 (t, J=4.6 Hz, 2H), 4.00 (m, 2H), 3.89 (m, 1H), 2.76-2.66 (m, 2H), 2.59-2.51 (m, 2H). MS (ESI): m/z=245 [M+H]+

Step D: Benzyl 3-(N-((cis)-3-(2,3-dihydropyrrolo[3',2':5,6]pyrido[3,4-b][1,4]oxazin-1(7H)-yl)cyclobutyl)sulfamoyl)azetidine-1-carboxylate (6)

To a stirred suspension of 6 (3.10 g, 9.77 mmol) in DMF (98 mL) was added DIPEA (8.51 mL, 48.9 mmol) to afford a solution and benzyl 3-(chlorosulfonyl)azetidine-1-carboxylate (7) (2.97 g, 10.26 mmol) in DMF (11 mL) was quickly added and the reaction mixture was stirred at r.t. for 1 h. Water was added and the aqueous layer was extracted twice with EtOAc. The combined organic layers were washed with brine and dried under $Na_2SO_4$, filtered and concentrated under vacuum to afford the crude product as an orange oil. The crude material was purified by silica gel column chromatography eluting with a gradient of 0-10% MeOH in DCM to afford the title compound (6) (3.96 g, 81%) as an orange solid.

1H NMR ($CDCl_3$) δ 9.42 (s, 1H), 7.74 (s, 1H), 7.35-7.26 (m, 5H), 7.18 (s, 1H), 7.10 (d, J=3.7 Hz, 1H), 6.42 (d, J=3.7 Hz, 1H), 5.09 (s, 2H), 4.60 (p, J=8.4 Hz, 1H), 4.28 (m, 4H), 4.17-4.07 (m, 2H), 3.98 (p, J=6.8 Hz, 1H), 3.79 (m, 1H), 3.41 (m, 2H), 2.69 (m, 2H), 2.24 (m, 2H). MS (ESI): m/z=498 [M+H]+

Step E. N-((cis)-3-(2,3-Dihydropyrrolo[3',2':5,6]pyrido[3, 4-b][1,4]oxazin-1(7H)-yl)cyclobutyl)-azetidine-3-sulfonamide (8)

A solution of benzyl 3-(N-((cis)-3-(2,3-dihydropyrrolo[3',2':5,6]pyrido[3,4-b][1,4]oxazin-1(7H)-yl)cyclobutyl)sulfamoyl)azetidine-1-carboxylate (3.66 g, 7.36 mmol) in EtOH (74 mL) was flushed with Ar before 20% $Pd(OH)_2/C$ (775 mg) was added. The reaction vessel was backfilled with $H_2$ and the reaction was stirred at 80° C. for 5 h. The mixture was filtered through a pad of Celite and the Celite was washed with EtOH (100 mL) and a mixture of EtOH/DCM 50:50 (20 mL). The filtrate was concentrated to dryness under vacuum to afford the title compound (2.74 g, 99%) as a yellow solid.

1H NMR (DMSO-d6) δ 11.98 (s, 1H), 8.12 (d, J=9.0 Hz, 1H), 7.82 (s, 1H), 7.33 (d, J=3.6 Hz, 1H), 6.87 (d, J=3.7 Hz, 1H), 4.78-4.65 (m, 1H), 4.42-4.31 (m, 3H), 4.27-4.23 (m, 2H), 4.19-4.07 (m, 2H), 3.73 (overlapping signals, 3H), 2.65 (m, 2H), 2.34 (qd, J=9.1, 2.4 Hz, 2H). MS (ESI): m/z=364 [M+H]+

Step F. 1-Cyclopropyl-N-((cis)-3-(2,3-dihydropyrrolo[3',2':5,6]pyrido[3, 4-b][1,4]oxazin-1(7H)-yl)cyclobutyl)azetidine-3-sulfonamide (Compound E)

N-((cis)-3-(2,3-Dihydropyrrolo[3',2':5,6]pyrido[3,4-b][1,4]oxazin-1(7H)-yl)cyclobutyl)azetidine-3-sulfonamide (1.2 g, 3.30 mmol), dry MeOH (21 mL), molecular sieves 3 Å (141 mg) and ((1-ethoxycyclopropyl)oxy)trimethylsilane (1.06 mL, 5.28 mmol) were combined in a sealable reaction vessel. The vessel was purged with argon and AcOH (944 μL, 16.51 mmol) was added. The vessel was sealed and heated at 80° C. for 2 h. After the mixture was cooled to room temperature, sodium cyanoborohydride (518 mg, 8.25 mmol) was added. The vessel was resealed and heated slowly to 40° C. for 1.5 h. Further $NaBH_3CN$ (260 mg, 4.16 mmol) was added and the reaction mixture was allowed to stir for 48 h. The crude mixture was filtered over Celite and washed with methanol. The filtrate was concentrated and the residue was taken up in an aqueous saturated sodium bicarbonate solution. The resulting solution was extracted with $CHCl_3$/iPrOH and the combined organic layers were washed with brine, dried over $Na_2SO_4$, filtered and concentrated to afford the crude product as a cream powder. The crude material was purified by silica gel column chromatography eluting with a gradient of 20:80 to 80:20 of Cyclohexane/(EtOAc/EtOH 3:1) and finally with a mixture of EtOAc/EtOH (3:1) 100%) to give the purified product. The solid obtained was suspended in EtOH (10 mL) and the mixture was sonicated affording a precipitate that was collected by filtration, washed with cold EtOH and powder was dried to a constant weight under vacuum to afford the title compound (0.661 g, 48%) as a white solid.

1H NMR (DMSO-d6) δ 11.15 (s, 1H), 7.63-7.54 (m, 2H), 7.16 (dd, J=3.6, 2.2 Hz, 1H), 6.55 (dd, J=3.7, 1.5 Hz, 1H), 4.59 (tt, J=9.6, 7.3 Hz, 1H), 4.09 (dd, J=5.2, 3.7 Hz, 2H), 3.98-3.86 (m, 1H), 3.69-3.56 (m, 1H), 3.53 (m, 2H), 3.51-3.45 (m, 2H), 3.39 (dd, J=8.1, 6.8 Hz, 2H), 2.58-2.51 (m, 2H), 2.23 (qd, J=9.0, 2.7 Hz, 2H), 1.92 (tt, J=6.7, 3.5 Hz, 1H), 0.40-0.30 (m, 2H), 0.24-0.16 (m, 2H). MS (ESI): m/z=404 [M+H]+.

Benzyl 3-(chlorosulfonyl)azetidine-1-carboxylate (7) used in the preparation of Compound E, was prepared following the scheme:

Scheme 2

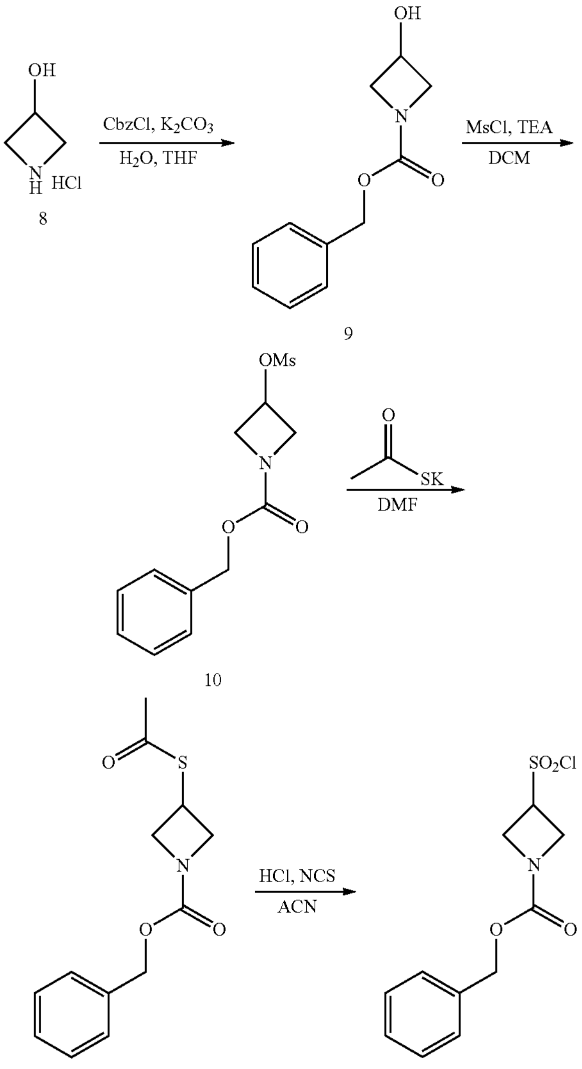

8 9 10 11 7

Step A: Benzyl 3-hydroxyazetidine-1-carboxylate (9)

To a solution of azetidin-3-ol hydrochloride (8) (60 g, 547.7 mmol) in anhydrous THF (720 mL) and $H_2O$ (360 mL) was added $K_2CO_3$ (151 g, 1095 mmol). The mixture was stirred at r.t. for 30 min then cooled to 0° C. CbzCl (97 g, 569.6 mmol) was then added slowly and the reaction mixture was stirred at r.t. overnight. The mixture was filtered. The solvent was removed in vacuo and the residue was taken up into EtOAc (500 mL) and $H_2O$ (300 mL). The organic layer was separated. The combined organic layers were washed with brine (200 mL), dried over $Na_2SO_4$ and filtered. The filtrate was concentrated under the reduced pressure to afford the compound 9 as an off-white solid (110 g, 96%).

1H NMR ($CDCl_3$) δ 7.36 (m, 5H), 5.09 (s, 2H), 4.61 (m, 1H), 4.23 (m, 2H, 3.88 (m, 2H), 2.55 (d, 1H). MS (ESI): m/z=208 [M+H]+

Step B: Benzyl 3-((methylsulfonyl)oxy)azetidine-1-carboxylate (10)

To a solution of 9 (110 g, 530.89 mmol) in anhydrous DCM (500 mL) was added TEA (53.7 g, 531 mmol). The mixture was cooled to 0° C. and MsCl (63.8 g, 557.43 mmol) was added dropwise. The mixture was stirred at 0° C. for 30 min under $N_2$ protection. Water (300 mL) was added to the mixture. The organic layer was separated. The combined organic layers were washed with aqueous $NaHCO_3$ (300 mL) and brine (200 mL), dried over $Na_2SO_4$ and filtered. The filtrate was concentrated under the reduced pressure to afford the compound 10 as an off-white solid (140 g, 92%).

1H NMR ($CDCl_3$) δ 7.35 (m, 5H), 5.23 (m, 1H), 5.11 (s, 2H), 4.36 (m, 2H), 4.18 (m, 2H), 3.06 (s, 3H). MS (ESI): m/z=286 [M+H]+

Step C. Benzyl 3-(acetylthio)azetidine-1-carboxylate (11)

To a solution of compound 10 (140 g, 490.69 mmol) in anhydrous DMF (1300 mL) was added potassium thioacetate (140.1 g, 1226.74 mmol). The mixture was stirred at 80° C. overnight under $N_2$ protection. The reaction was cooled to r.t. and poured into water (1 L). The aqueous layers were extracted with EtOAc (3×200 mL) and the combined organic layers were washed with brine (300 mL), dried over $Na_2SO_4$ and filtered. The filtrate was concentrated under the reduced pressure. The residue was purified by column chromatography on silica gel (petroleum ether/ethyl acetate=5/1) to afford 11 as an off-white solid (70 g, 53%).

1H NMR ($CDCl_3$) δ 7.34 (m, 5H), 5.09 (s, 2H), 4.45 (m, 2H), 4.21 (m, 1H), 3.90 (m, 2H), 2.33 (s, 3H). MS (ESI): m/z=266 [M+H]+

Step D: Benzyl 3-(chlorosulfonyl)azetidine-1-carboxylate (7)

A solution of NCS (130.8 g, 979.91 mmol) in a mixture of anhydrous MeCN (800 mL) and conc. HCl (209 mL) was stirred at r.t. for 30 min. The reaction mixture was then cooled to 0° C. and a solution of compound 11 (65 g, 244.98 mmol) in MeCN (200 mL) was added slowly to the mixture. The mixture was stirred at 0° C. for 30 min under $N_2$ protection. The reaction mixture was diluted with sat. $NaHCO_3$ and extracted with DCM (3*200 mL). The combined organic layers were washed with brine (300 mL), dried over $Na_2SO_4$ and filtered. The filtrate was concentrated under the reduced pressure. The residue was purified by column chromatography on silica gel (petroleum ether/ethyl acetate=5/1) to afford compound 7 as a white solid (53 g, 74%).

1H NMR ($CDCl_3$) δ 7.35 (m, 5H), 5.13 (s, 2H), 4.54 (m, 1H), 4.44 (m, 4H). MS (ESI): m/z=291 [M+H]+.

Other compounds can be similarly prepared using the appropriate intermediate compounds.

Biological Assay

Exemplary biological assays are described below and the results are summarized in Table 1.

Example 2: In Vitro Enzyme Assay

Kinase assays using a recombinant enzyme, biotinylated substrate, and ATP were performed as described by the manufacturer (Cisbio). Kinase reaction was performed in a 10 μL volume using low-volume ProxiPlate 384-well plates (Perkin Elmer, 6008280). The 1× Kinase reaction Buffer (KRB) consisted of 50 mM TRIS pH 8.0, 0.01% Tween 20, 10 mM $MgCl_2$, and 2 mM DTT. Recombinant JAK1 (Life Technologies, PV4775), JAK2 (Life Technologies, PV4210), JAK3 (Life Technologies, PV3855), and Tyk2 enzyme (Life Technologies, PR8440C) were used at a final concentration of 2.7 nM, 2 pM, 24 pM and 350 pM respectively. These amounts of JAK proteins were determined as to insure initial velocity and linearity over time. The enzyme buffer solution was prepared by adding 25% Glycerol and 250 nM SEB (Cisbio) to the 1× Kinase reaction buffer. Briefly, 4 μl of 2.5× compounds in DMSO (final DMSO concentration at 0.2% in KRB buffer) were added to each well, followed by 2 μl of 5× TK substrate-biotin (Cisbio, final concentration of 1 μM in KRB buffer) per well. Next, 2 μl of 5× kinase were added, followed by 2 μl of 5×ATP (Sigma, final concentration of 300 μM in KRB buffer). After a 30-min incubation at 23° C., 10 μl/well of a mix containing the streptavidin XL-665 (Cisbio, final concentration at 125 nM in the detection buffer) and TK antibody-cryptate (Cisbio, 1× final concentration in the detection buffer). The plate was incubated for one h at 23° C. and read on the Envision reader (Perkin Elmer) at wavelengths of 337 nM for the excitation and 620 nM and 665 nM for the emission. Compounds were tested in duplicates over 10 three-step dilutions in order to determine their $IC_{50}$ values against the four enzymes. The ratio between the acceptor (665 nM) and donor (620 nM) emission was used to calculate $IC_{50}$.

Example 3 In Vitro Cellular Assay

-pSTAT3 assay (MSD Phospho-STAT3 (Tyr705) kit, K150SVD): TF-1 cells (CRL-2003, ATCC) were starved at high concentration (15×106 cells/flask), in T75 flasks containing reduced-serum and phenol re-free Opti-MEM (Thermofisher, 11058-021). The flasks were incubated overnight at 37° C., 5% $CO_2$ then seeded in 96 well plates (TPP) at 150000 cells/well in 25 μL. Cells were treated with 5 IL/well of serially diluted compounds in DMSO (final DMSO concentration of 0.1%) and incubated for 30 min at 37° C. IL-6 (6 IL/well, 100 ng/ml as a final concentration in Opti-MEM, Thermofisher, PHC0066) was added to the cell plates and followed by a 30-min incubation at 37° C. Next, cells were lysed by adding 12 μl/well of 4× supplemented lysis buffer, incubated at 4° C. for 30 min under agitation. The samples were processed for the pSTAT3 detection as described by the manufacturer (MSD) with 25 μl of nondiluted cell lysates tested. Compounds were tested in simplicates over 10 three-step dilutions in order to determine their $IC_{50}$ values.

-pSTAT5 assay (Live Blazer FRET—B/G Loading kit, Life Technologies): Irf1-bla TF-1 (Life Technologies, K1657) were starved at high concentration (12×106 cells/flask), in T75 flasks containing reduced-serum and phenol re-free Opti-MEM (Thermofisher, 11058-021) with 0.5% dialyzed FBS. The flasks were incubated overnight at 37° C., 5% $CO_2$ then seeded in 384 well plates at 30000 cells/well in 32 μL. Next, 4 μl of 10× compounds serially diluted in DMSO (final DMSO concentration of 0.1%) were added to the cells and incubated for 30 min at 37° C. Then, 4 μl of 10× GM-CSF (final concentration 1 ng/ml in Opti-MEM, Thermofisher, PHC2015) was added and incubated for 5 h at 37° C. Finally, 8 μl of the 6× LiveBlazer-FRET substrate (was added to the wells and incubated for 2.5 h at room temperature in the dark. The plate was read on the Envision reader (Perkin Elmer) at wavelengths of 409 nM for the excitation and 450 nM and 520 nM for the emission. Compounds were tested in duplicates over 10 three-step dilutions in order to determine their $IC_{50}$ values. The ratio between the acceptor (450 nM) and donor (520 nM) emission was used to calculate the $IC_{50s}$.

Example 4: In Vivo Pharmacodynamy Model

-IL-6 induced Phospho-STAT3 model: BALB/c ByJ Rj mice were anesthetized by inhalation of isoflurane prior to Elizabethan collar application, treatment, and injection with IL-6. Test compounds (0.01-10 mM) or its vehicle (Propylene Glycol/Acetone/Transcutol (30/40/30, v/v/v)) were administered topically 2 h before an intravenous injection of mouse recombinant IL-6 (8 ng/g, R&D Systems). The control group was injected with saline and treated with vehicle only. Skin samples were harvested 15 min. The expression of p-STAT3Y705 and STAT3 will be quantified by MesoScale Technology in skin lysates relative to the group injected with saline and treated with vehicle (Meso Scale Technology™).

Example 5: Human Skin Ex Vivo

Flux through skin and dermis concentration were measured during 6-24 h ($ng/cm^2/h$) after disposition of the test compound 2.7 mM in PG/$H_2O$ cream 1 mg/mL. Human dermatomed skin (frozen), 350-500 μm thick were used in diffusion cells system Franz cells 1.76 $cm^2$ maintained at 32±1° C. after equilibration. Skin integrity was confirmed by TEWL <20 $g/m^2/h$. 3 donors were used for each test. The compound was formulated in modified aqueous British pharmacopoeia cream pH6 PG 14% and applied 5 $mg/cm^2$ by weighing. Receptor fluid containing 4% BSA in PBS 10 mM was maintained under agitation and was sampled along with dermis sampled at 6 h and 24 h after exposure. 5 Strips were used to remove carefully the excess of formulation and were not dosed.

Example 6: Protein Binding Analysis

The protein binding was assessed in plasma of Human, male balb-c mice, male Wistar Han rat, male Göttingen minipig by rapid equilibrium dialysis (RED) devices. After the plasma and buffer phosphate 50 mM pH7.4 were equilibrated at 37° C., the compound was added to plasma to reach a final concentration of 5 μM. An aliquot of plasma was withdrawn immediately. Equilibration under mild agitation was continued for 4 h. The plasma and buffer were sampled and samples were quenched with 4 volumes of acetonitrile and centrifuged. Supernatant was quantified in HPLC/MS/MS to calculate the recovery and the percentage of compound dissolved in the buffer (unbound) and bound to plasma proteins.

Example 7: Intrinsic Clearance in Hepatocytes of h-r-m-Minipig

The intrinsic clearance was assessed in cryopreserved Hepatocytes obtained by Human livers donors of mix gender pooled together, male balb-c mouse, male Wistar Han rats and male Göttingen minipig, by looking at the parent compound disappearance. The incubations were performed using a final concentration of viable cells of 1 million/ml (viability above 70%) and test item of 2.5 μM. Incubations were followed up to 2 h. Aliquotes were withdrawn at different time points and reaction quenched with acetonitrile. After centrifugation the supernatant was analyzed by HPLC/MS to quantify the remaining amount of parent in comparison with time 0. The clearance was calculated by fitting the log of the percentage remaining with Graphpad Prism ver.7.

Example 8: Activity of Metabolites

The potential of test item's metabolites to be active was assessed in the cellular assay looking at phosphorylation of Stat3. Test item was incubated with human liver microsomes for 0 min (freezed pending further processing) or 2 h at different concentration ranging from 0.5 to 10000 nM. At the end of the incubation the supernatant was removed by centrifugation and 1 μl was added to the cells and processed as in the regular assay while another aliquot was used to determine the remaining concentration of the test item. The $IC_{50}$ obtained with supernatant from the time 0 set of incubations was compared with the one obtained with the set at 2 h calculated using nominal test item concentrations. If metabolism was negligible or the pool of metabolites were equipotent to the parent, the two $IC_{50}$s were expected to be the same, i.e. ratio of 1. On the contrary, if metabolism was relevant and all metabolites were devoid of any activity, the $IC_{50}$ of the 2 h set was expected to be a multiple of the one without metabolites and to be estimated by the parent residual concentration.

Example 9: CYP2D6 and 3A Inhibition

The potential to inhibit CYP2D6 and 3A was assessed in Human pooled liver microsomes of mixed gender (mainly Caucasian) assessing the $IC_{50}$ of Compound E on selective probe substrates: dextromethorphan for CYP2D6 and midazolam & testosterone for CYP3A. After 5 min at 37° C. incubations were started with NADPH and prolonged for 10 min. The test compound was tested up to 30 μM keeping the final concentration of organic solvent was below 0.5%. The final concentration of microsomes was 0.1 mg/ml to ensure linearity during the time of the incubation. The reaction was quenched by adding 3 volume of acetonitrile. After centrifugation the supernatant was analyzed by HPLC/MS/MS for the formation of des-methyldextromethorphane selectively produced by CYP2D6 and 1'hydroxymidazolam or 6p-hydroxytestosterone, selectively produced by CYP3A. $IC_{50}$ was calculated with Graphpad Prism v.7 comparing the amount of metabolite produced in presence of the test compound with that produced in absence of test item.

Example 10: In Vivo Pharmacokinetic Analysis in Rat

One male Wistar Han rat. Compound was administered intravenously to fed animal at a target dose of 1 mg/kg, dose volume: 2 mL/kg, in DMSO/hydroxypropyl-beta-cyclodextrin 20% in phosphate buffer 60 mM pH 7 (5:95). Blood samples were collected at various time points. Blood samples were then assayed using a method based upon protein precipitation with acetonitrile followed by LC/MS/MS analysis. Non-compartmental methods were used for pharmacokinetic analysis of blood concentration versus time data Example 11: In Vivo Pharmacokinetic Analysis in Minipig Three male Göttingen minipigs. Compound was administered intravenously to fed animals at a target dose of 1 mg/kg, dose volume 1 mL/kg, in DMSO: hydroxypropyl-p-cyclodextrin 20% in phosphate buffer 60 mM pH 7 (5:95). Blood samples were collected at various time points. Blood samples were then assayed using a method based upon protein precipitation with acetonitrile followed by LC/MS/MS analysis. Non-compartmental methods were used for pharmacokinetic analysis of blood concentration versus time data.

Example 12: Eurofins Protocol

Human full skin samples from abdominal surgery. Excess subcutaneous fat will be removed when necessary. Skin samples were excised and cut into pieces of approximately 2.5 cm×2.5 cm. Full skin was used and the thickness measured by Oditest calipers.

After sufficient equilibration time in the Franz cell, the stratum corneum integrity was measured for each full skin sample by TransEpidermal Water Loss (TEWL) using Tewameter in the range of 0.5-5 g/m2/h (1). The diffusion chamber and skin samples were maintained at a constant temperature of 32 f 1° C. The compounds were formulated 10 mM in Vehicle PG/Ethanol 30/70 (w/w) freshly the day of the test and applied per cell (2 $cm^2$) 5 $\mu L/cm^2$ corresponding to 10 μL applied (theoretical amount applied 0.1 μmol). 2 cells per donors per test were used.

The diffusion cells will be placed on a magnetic stirrer, which will be integrated with a water bath maintained at a temperature of 32° C. 1° C. Cells will be identified by a letter. The receptor compartment of each cell will be filled with the receptor fluid in such a way to prevent any formation of air-bubbles and with a sufficient amount in order to obtain a meniscus slightly above the brim of the compartment. The receptor fluid PBS pH7.2+0.25% Tween 80 is pre-warmed before to mount the cells. The skin samples are placed on the receptor compartment. The donor compartment is placed onto the skin samples. After checking the absence of air-bubbles, a clamp is placed to link both compartments. Agitation of receptor fluid is started.

Example 13: Mini Ames Assay (TA98 and TA100)

The Ames test in micro-method (in 6-well plates=mini Ames) follows the general principles of the standard Ames's technique. The Ames test used strains of bacteria *Salmonella typhimurium* that carry mutations in the genes involved in histidine synthesis. These strains are auxotrophic mutants, they require histidine for growth but cannot produce it. The assay was used to observe the ability of the test item to induce reverse mutations allowing the bacteria to grow in a histidine-free medium. The number of bacteria that revert and acquire the wild-type ability to grow in the absence of histidine can be estimated by counting the colonies that develop upon incubation. The use of different strains allows the identification of different mechanisms of gene mutation (TA98 for detection of frameshift mutations and TA100 for detection of base pair substitutions).

In a number of cases, the test item itself is not directly mutagenic but its metabolic derivatives are. Therefore, the test items were studied on TA98 and TA100 with or without metabolic activation (S9) in order to demonstrate promutagens and direct mutagens.

A toxicity assessment was performed on complete nutriment agar plate (with histidine) to define the highest concentration to be used in the genotoxicity assay. Solutions were prepared in 100% DMSO. The first concentration analyzed in the well (6-well plate) was 500 μg per plate followed by 7 serial dilutions (2 times factor of dilution). Each concentration was tested in triplicate on each strain and for each condition of treatment. The viability of the positive and negative controls was analyzed for each strain, in the presence or absence of metabolic activation system, and were compared with historical data to validate the study. If no bacterial toxicity occurred, the highest concentration tested for genotoxicity was 1000 μg per plate. If toxicity occurred, a viability above than 70% defined the highest concentration tested.

The genotoxicity assessment was performed on minimal agar plate (without histidine) following the same dilution procedure as for the cytotoxicity assessment. DMSO and phosphate buffer controls were used as negative controls. 2-Nitrofluorene (2NF), 2-Aminoanthracene (2AA) and 4-Nitro-1.2 phenylenediamine (DANB) were selected as positive controls.

Test items, positive and negative controls were incubated with the 2 bacterial strains. After 48 h incubation at 37° C. with and without metabolic activation (S9), the prototrophic mutant colonies that had grown on the plates were counted. The results were expressed as the mean number of revertants for each condition tested (3 replicates each) and for each concentration of the test item and controls. Induction ration, corresponding to the ratio of revertants in presence of test item versus spontaneous revertant, was determined for each concentration. A test article was considered mutagenic when a concentration-related increase over the range tested and/or a reproducible increase at one or more concentrations in the number of revertant colonies per plate was observed in at least one strain with or without metabolic activation system.

The results indicated that Compound E did not induce a biologically significant increase in the mean number of revertants on the *Salmonella typhimurium* TA98 and TA 100 with or without metabolic activation. Therefore, the Compound E was not considered to be mutagenic under the experimental conditions for TA98 & TA100 (with and without metabolic system).

Example 14: $IC_{50}$ Determination on 6 Tyrosine Kinases and 8 Serine/Threonine Kinases The test compound was dissolved in and diluted with dimethyl sulfoxide (DMSO) to achieve 100-fold higher concentration. The solution was further 25-fold diluted with assay buffer to make the final test compound solution. Reference compounds for assay control were prepared similarly.

Target kinases were: FLT3_1 mM, JAK1_1 mM, JAK2_1 mM, JAK3_1 mM, RET_1 mM, TYK2_1 mM, AurA_1 mM, AurB_1 mM, AurC_1 mM, MAP2K1_Cascade, MAP2K4_Cascade, MAP3K2_Cascade, MNK2, ROCK1_1 mM.

The 4× Substrate/ATP/Metal solution was prepared with kit buffer (20 mM HEPES, 0.01% Triton X-100, 5 mM DTT, pH7.5), and 2× kinase solution was prepared with assay buffer (20 mM HEPES, 0.01% Triton X-100, 1 mM DTT, pH7.5). The 5 μL of 4× compound solution, 5 mL of 4× Substrate/ATP/Metal solution, and 10 mL of 2× kinase solution were mixed and incubated in a well of polypropylene 384 well microplate for 1 or 5 h* at room temperature. (*=depending on the kinase). 70 mL of Termination Buffer (QuickScout Screening Assist MSA; Carna Biosciences) was added to the well. The reaction mixture was applied to LabChip™ system (Perkin Elmer), and the product and substrate peptide peaks were separated and quantitated. The kinase reaction was evaluated by the product ratio calculated from peak heights of product (P) and substrate(S) peptides (P/(P+S)).

The readout value of reaction control (complete reaction mixture) was set as a 0% inhibition, and the readout value of background (Enzyme (−)) was set as a 100% inhibition. The percent inhibition of each test solution was calculated. $IC_{50}$ value was calculated from concentration vs. % Inhibition curves by fitting to a four parameter logistic curve. The concentration vs. % inhibition curve for JAK1_1 mM for the control and the tested compounds is depicted in FIG. 1.

Example 15: CEREP Safety Screen-44

An in vitro pharmacology assay was conducted to assess the capability of the compounds to interact with different pharmacological targets when tested at 10 μM in different binding and enzyme/uptake assays. The included targets are indicative of potential effects in major organs and drug-drug interactions.

Compound binding was calculated as a % inhibition of the binding of a radioactively labelled ligand specific for each target. Compounds were tested at 1.0E-05 M. Compound enzyme inhibition effect was calculated as a % inhibition of control enzyme activity. Results showing an inhibition or stimulation higher than 50% are considered to represent significant effects of the test compounds.

Figure 2:
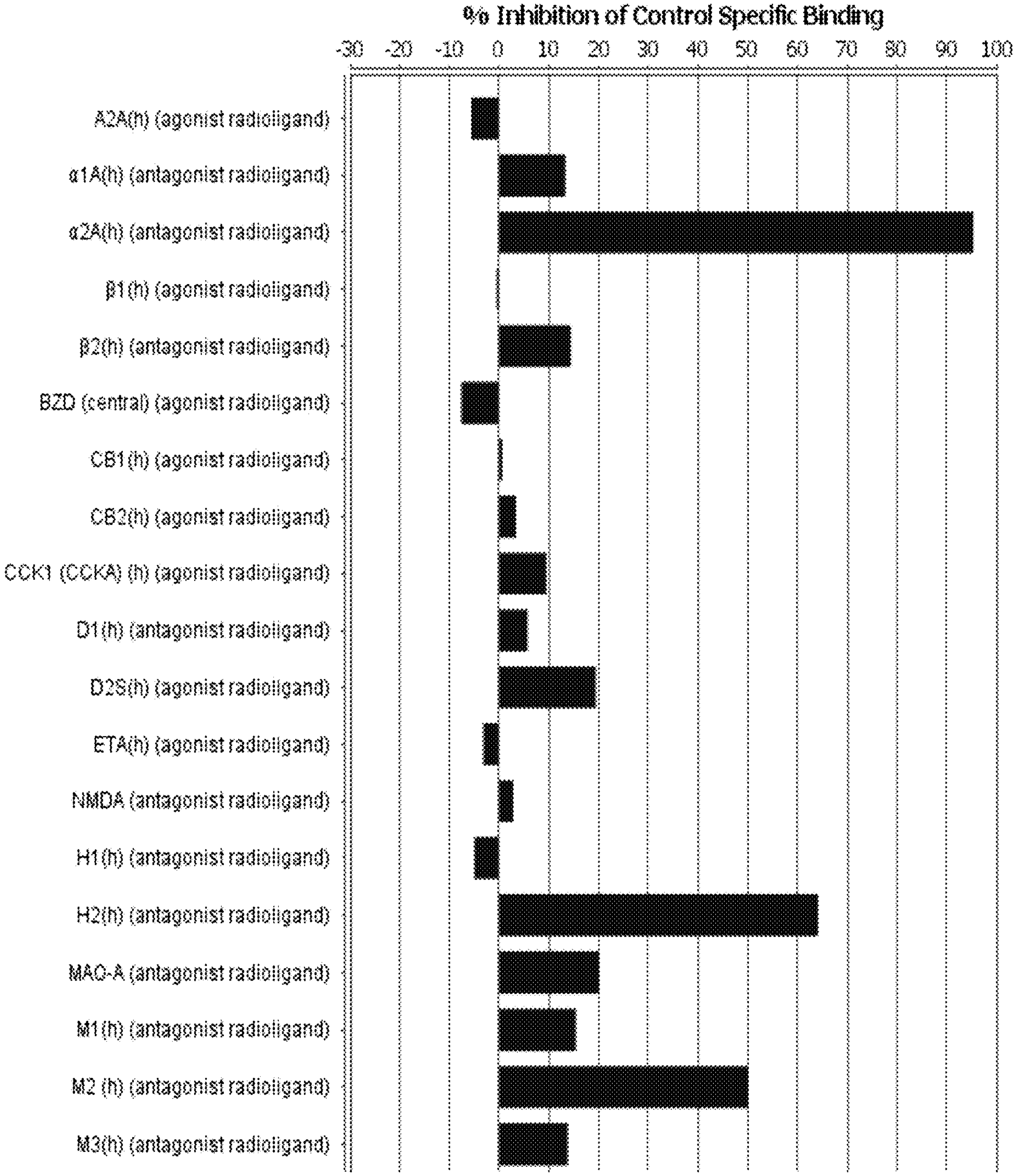
FIG. 2 illustrates the histogram plots for in vitro binding assay of Compound E to various receptors.
Figure 2:
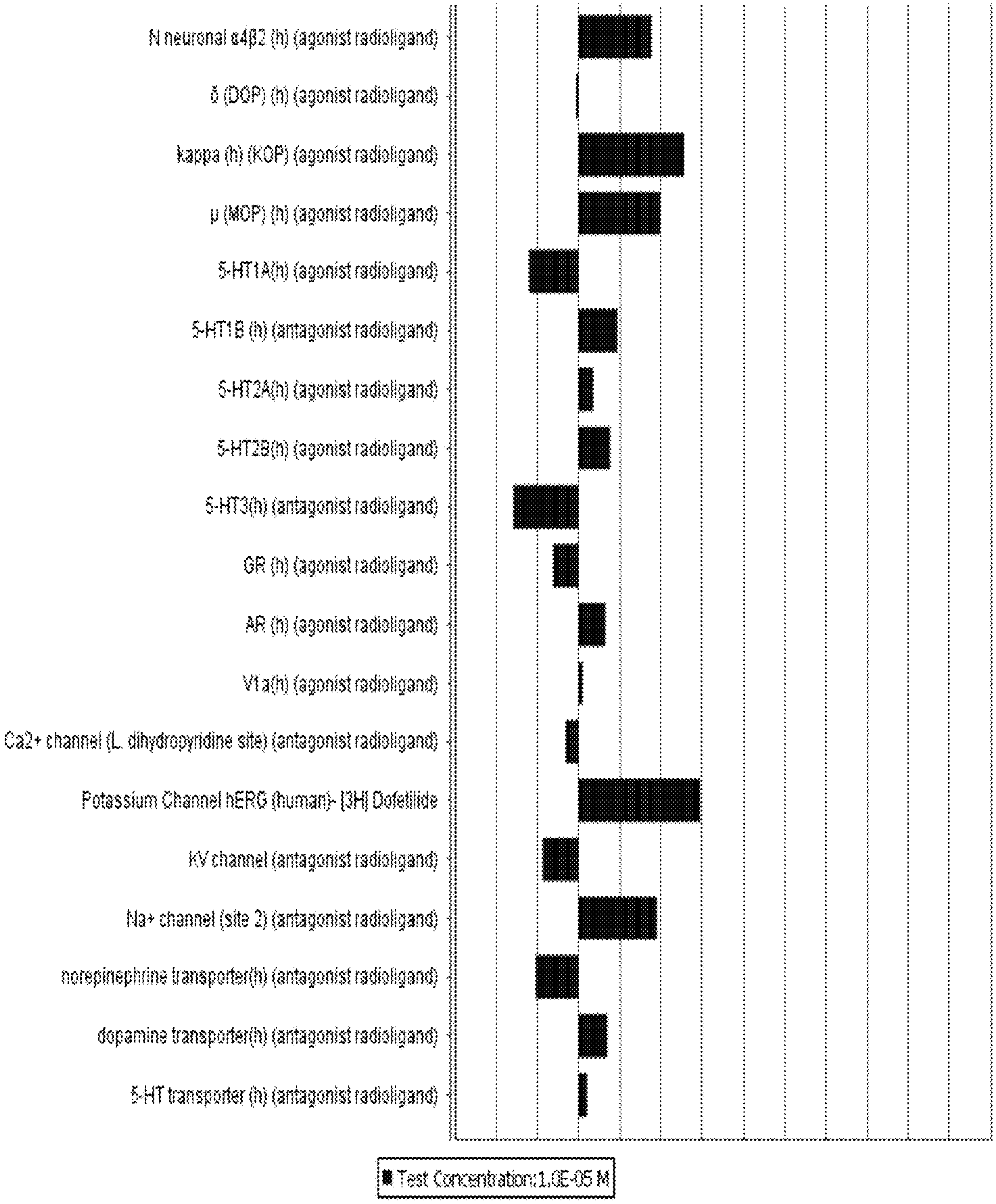
Figure 3:
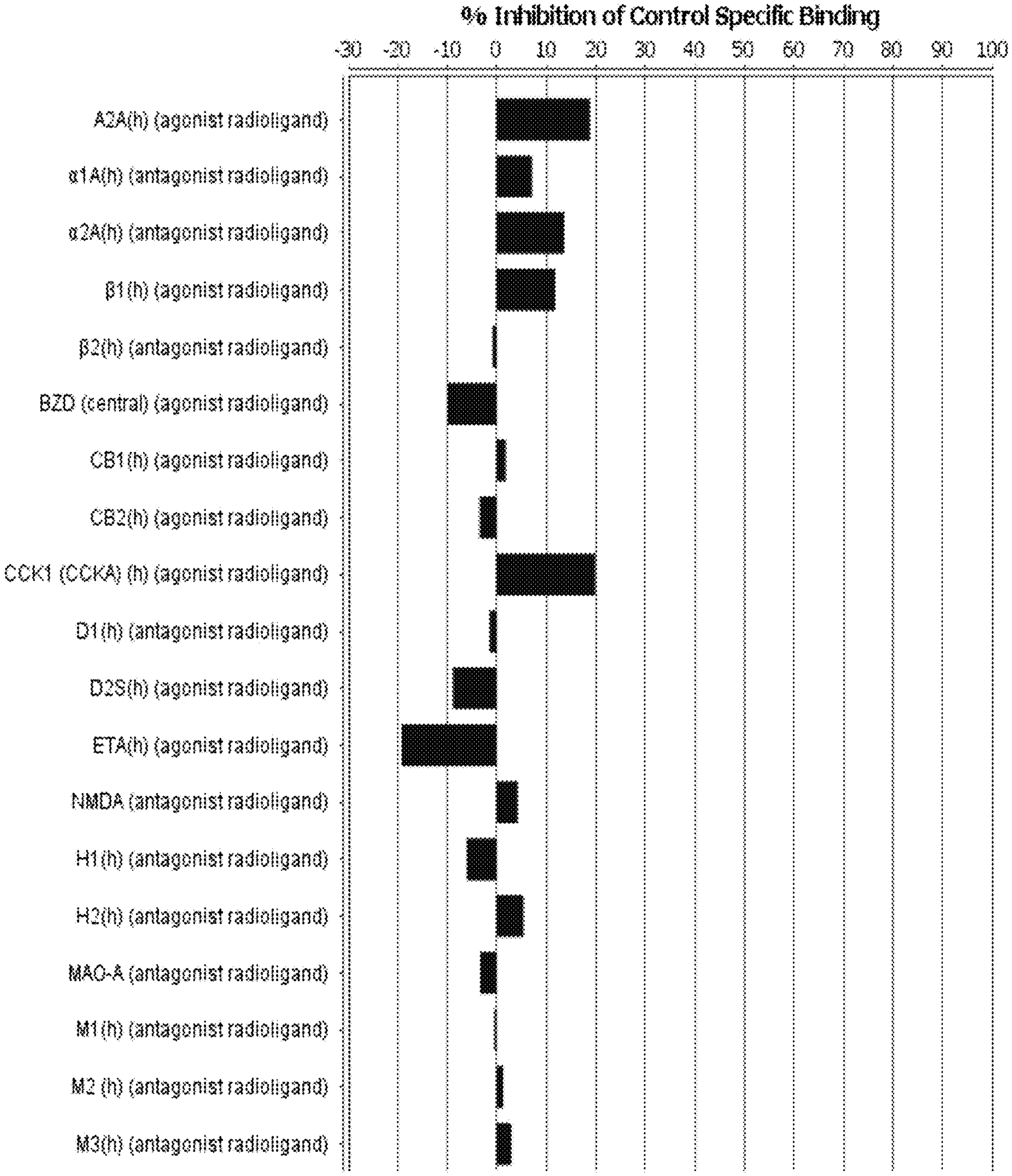
FIG. 3 illustrates the histogram plots for in vitro binding assay of Ruxolitinib to various receptors.
Figure 3:
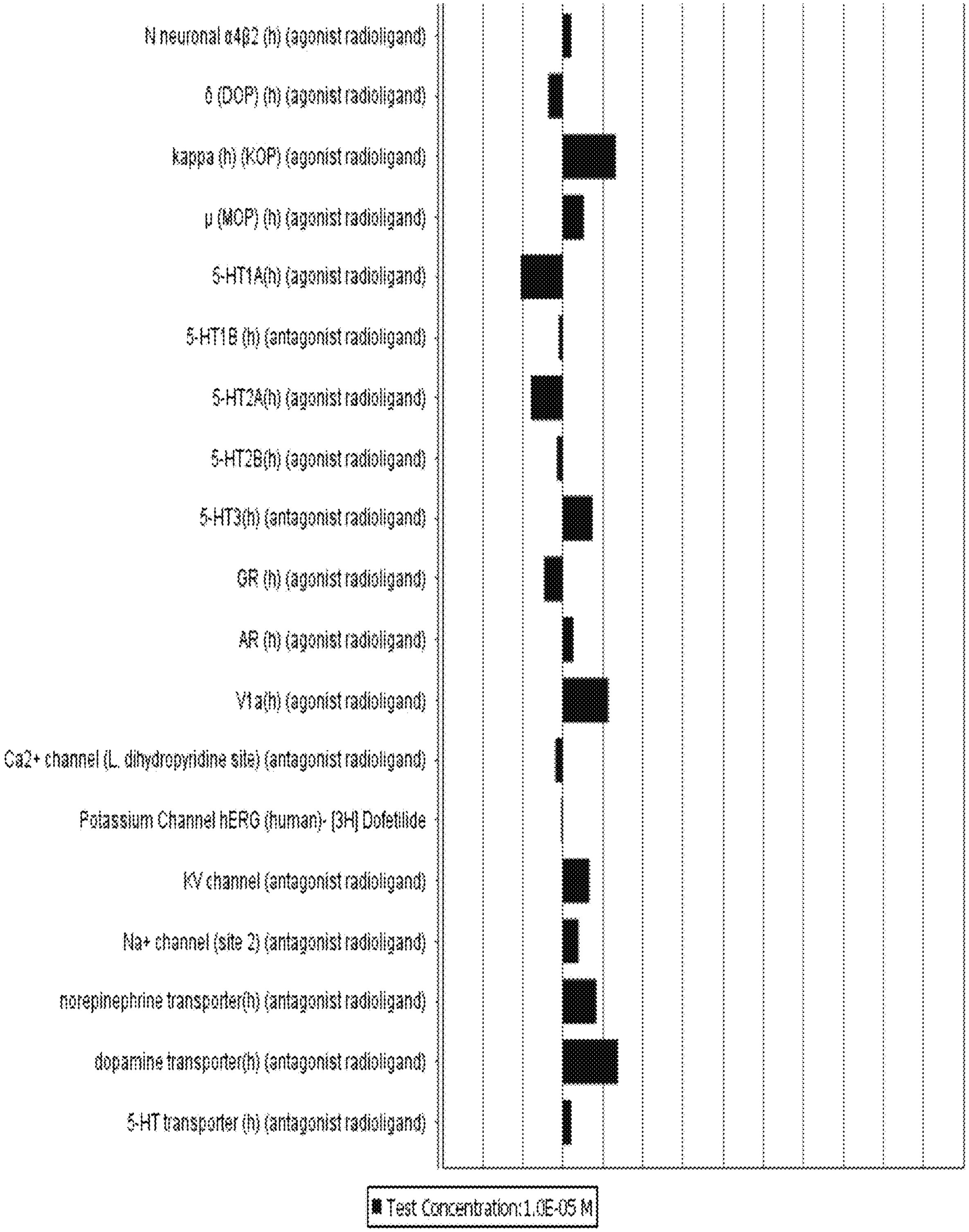
Figure 4:
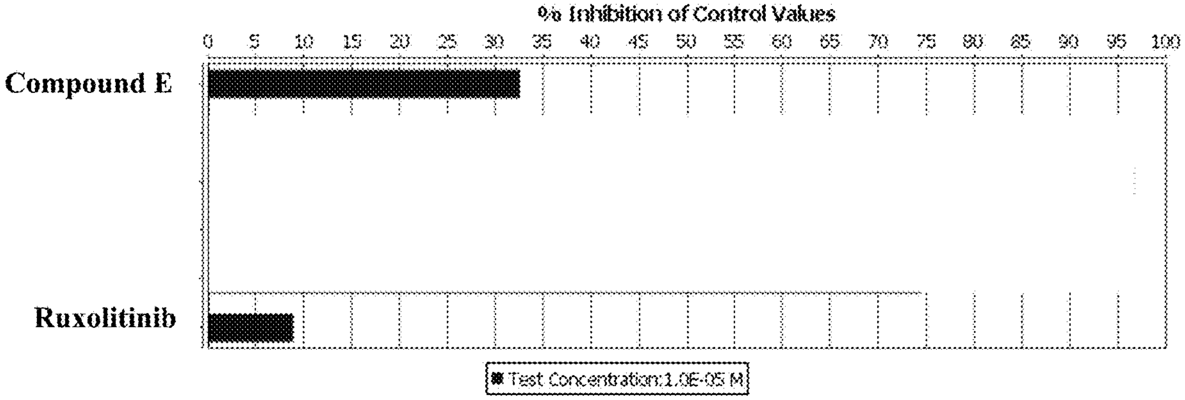
FIG. 4 illustrates the histogram plots for in vitro acetylcholinesterase (h) binding assay of Compound E and Ruxolitinib.

The results are as shown in FIGS. 2-4. Specifically, FIG. 2 depicts the histogram for Compound E and FIG. 3 depicts the histogram for Ruxolitinib. Further, FIG. 4 is a histogram for acetylcholinesterase (h) showing % inhibition for Compound E, and Ruxolitinib. It can be seen that Compound E shows significantly improved pharmacological effects over Ruxolitinib.

Example 16: In Vitro Human Lymphocyte (TK6) Micronucleus Assay

The objective of the test is to evaluate the clastogenic and aneugenic potential of the tested compound by its effects on the frequency of micronuclei in Human lymphoblast TK6 cells.

Compounds were tested for cytotoxicity in a range of concentrations following 3-hour and 26-hour treatment without metabolic activation-mix. Cell viability was measured by the relative population doubling (RPD) value. Top concentrations for micronucleus analysis were selected according to the 40 to 50% RPD acceptance criteria (RPD≥40%) for the short-term and long-term treatment.

For the micronucleus analysis, compounds were incubated with TK6 cells for 3 h in the presence and absence of S9 and for 26 h in the absence of S9. Vehicle was used as negative control and Mitomycin C and Vinblastine as positive controls. Micronuclei incidence was expressed as micronucleated mononucleated cells frequency per 1000 cells. The assay was considered positive when the incidence of micronucleated cell exceeded the historical value and was concentration-related.

For clastogenicity and aneugenicity evaluation the telomere and centromere staining used PNA probes to the automatic scoring of MN. This information provided by telomere and centromere staining allowed determination of the nature of the agent: clastogenic (MN with telomere signal, as well as MN without any signal) or aneugenic (MN with telomere and centromere signal).

Example 17: In Vitro hERG Channel

Blockade of the delayed rectifier potassium current (IKr) encoded by hERG gene (human ether a go go-related gene) can lead to QT interval prolongation and is therefore investigated as part of the cardiac risk assessment. This channel is critical for the repolarisation of the cardiac membrane. The effect of the compounds on IKr was assessed by whole cell patch clamp in stably transfected CHO-K1 cells expressing hERG (Human Ether-a-go-go Related Gene) channel following superfusion at different concentrations up to 30 μM.

Example 18: Phototoxicity

Phototoxicity was evaluated in 3T3 murine fibroblasts. Cells were incubated with different concentrations of test compounds. One plate was then exposed to a dose of 7 J/cm2 (UVA/UVB mimicking usual solar exposure) whereas the other plate was kept in the dark. The treatment medium was then replaced with culture medium and after 24 h cell viability was determined by Neutral red uptake. Concentration leading to 50% decrease of viability was calculated in the absence and in the presence of irradiation. The PIF (photo irritation factor) ratio was then calculated: PIF=IC50+UV/IC50−UV).

Other studies including, but not limited to, $CaCO_2$ permeability, metabolite profiling in human microsomes (Syneos 7007703.SA.186) and in human hepatocytes (Syneos 7007703.SA.185), metabolite M3b structural elucidation (Syneos 7007703.SA.186), mouse iv female (ODS CFH-1798), mouse iv+ABT females (ODS CFH 1799), mouse topical d1,d10 (ODS Study Number: NBK39-32, 12 Sep. 2019, ELN Bioanalysis study: NBK156-79), rat iv (Pharmaron PH-DMPK-GAL-20-002), dog topical d1, d10 (CRL FY19.085) and minipig topical PK dl, d7 (Pharmaron 92404-19-914) are also conducted using the standard protocols known in the art.

The results of the biological assays for Example Compound E in comparison with Ruxolitinib is presented in Table 1 below. The results show that similar activity was observed for the tested compounds and Ruxolitinib in biochemical & cellular assays. The tested compounds of the present technology also show higher inhibitory activity and higher selectivity for JAK1, higher selectivity vs. JAK2 and higher selectivity vs. JAK3 and TYK2. Further, compared with Ruxolitinib, the tested compounds of the present technology also show similar or improved pharmacodynamic activity by topical route, skin penetration potential, safety profile and topical formulability.

All publications, patents, and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

TABLE 1

| | Ruxolitinib | Compound E |
|---|---|---|
| Enzymatic assay: $IC_{50}$ JAK1 (nM)/Ratio JAK2_JAK1/JAK3/Tyk2 | 8/0.2/252/27 | 9/48/>10000/3447 |
| Cellular Assay: $IC_{50}$ IL6 (nM)/Ratio | 8/2 | 9.9/44 |
| GMCSF_IL6 | 200 | 43 |
| Free $IC_{50}$ | 6.9/>1.5 | 1.6/>6.1 |
| hWB assay: $IC_{50}$ IL6 (microM)/Ratio GMCSF_IL6 | | |
| PD/IL6 mouse top @1 mM % inh vs vehicle (PG/EtOH 3/7) % inh/% vs Tofa | 60%/0.92 | 63%/0.97 |
| Activity | | |
| MW/TPSA/Chrom logD pH 7.4/ | 306/83/1.5 | 403/99/0.8 |
| SF logD/pKa | 2.3/3.7 | 2.1/5.3; 6.1 |
| c_FLUX/measured flux 6-24 hr (vs Ruxo) ($ng/cm^2/hr$)/dermis concentration (vs Ruxo) (microM) in PG/$H_2O$ cream 1 mg/mL | 6.6/5.3/1.9 (1) | 0.2/<0.24 (<0.04)/2.2 (0.9) |
| Kinetic aq sol/Thermodynamic sol PG_H2O pH 6 2/8 microM (mg/mL) | 232/ND (no cristalline material available - 1 mM (0.3 mg/mL)-amorphous) | 225/ND/TBD |
| Topical | | |
| hFU/rFU/mFU/minipig FU (%) | 4/13/7.7/25 | 23/16/28/32 |
| Intr. Clear. h heps/rheps/mheps/minipig heps | 4.4/300/150/141 | 6.5/40/28/44 |
| (microL/min/10 6 cells) | ? | 46/19 |
| Predicted hER/hCl/Vd/t½ | ND | 8/0.67 * |
| Pool metabolite activity: cell IL6 T0-&T2+: ratio/ vs CD16560 (100%) | | |
| Nber of metabolites | | 9 |
| microsomes | | 3 |
| hepatocytes | | <50% PP; NH(Compound E (x226- |
| comments on Met Id | | IL6); hClheps < 5) |
| iv PK rat: Cl/Vd/t½/ER | 40(51%)/ / / | (iv PK mice: 140/2.6/0.44/146_iv/iv: 0.4) |
| Rat In vitro/ in vivo correlation | 1.8 | 52(67%)/1.8/0.39/67 |
| iv PK minipig: Cl/Vd/t½/ER | 19(68%)/ / / | 0.6 |
| Minipig in vitro/in vivo correlation | 1.3 | 48(171%)/ / / |
| | | 0.4 |
| PD/IL6 mouse top DR 0.01-10 mM (PG/Acetone/Transcutol): | 81 nM | 185 nM |
| Systemic level @10 mM - 2 hrs | | |
| Systemic | | |
| $IC_{50}$ CYP2D6/CYP3A4 mid. & testo. (microM) | >30/>30/>30** (CRL data) | 20/ /5** (CRL data) |
| Selectivity $S_{35}$ @ 10 µM (S1) | 0.303 (0.042) — | 0.13 (0.002) - 1/403 |
| AMES/Phototox | | Neg/Neg |
| $IC_{50}$ hERG (microM) | | 15 |
| Safety panel (Cerep): 44 targets | 0/44 | 2/44 |
| % inh @10 microM | | (H2 (antago)-alpha2A (antago)) |
| Nb of targets > 50% inh | | |

ND = not determined;

TBD = to be determined,

What is claimed is:

1. A compound of formula (I), a salt thereof, or an enantiomer thereof, (I)

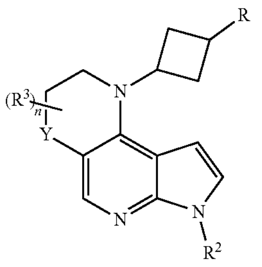

wherein:

Y is O, S, N or —CH;

R is a hydrogen atom, an alkyl group, a substituted alkyl group, an alkenyl group, a substituted alkenyl group, an alkynyl group, a substituted alkynyl group, —$OR^a$, —$NO_2$, —$C(O)R^b$, —$C(O)OR^a$, —$C(O)NR^cR^d$, —$SR^a$, —$S(O)R^b$, —$S(O)_2R^b$, —$S(O)NR^cR^d$, —$S(O)_2NR^cR^d$, —$NR^cR^d$, —$NR^cC(O)R^b$, —$NR^cC(O)NR^cR^d$, —$NR^cC(O)OR^a$, —$NR^cS(O)_2R^b$, —$NR^cS(O)_2NR^cR^d$, —$NR^cNR^cR^d$, —$NR^cNR^cC(O)R^b$, —$NR^cNR^cC(O)NR^cR^d$, —$NR^cNR^cC(O)OR^a$, —$CR^cR^dS(O)_2R^b$, —$CR^cR^dS(O)_2NR^cR^d$, —$OR^a$, —$OC(O)R^b$ or —$OC(O)NR^cR^d$;

$R^2$ is a hydrogen atom, an alkyl group or a substituted alkyl group, an alkenyl group, a substituted alkenyl group, an alkynyl group, a substituted alkynyl group, an aryl group, a substituted aryl group, a heterocyclic radical group, or a substituted heterocyclic radical group;

$R^3$ is independently selected from a hydrogen atom, an alkyl group, a substituted alkyl group, an alkenyl group, a substituted alkenyl group, an alkynyl group, a substituted alkynyl group, an alkoxy group, a haloalkyl group, a halogen, a cycloalkyl group, a substituted cycloalkyl group, —CN, —$NO_2$, —$C(O)OR^a$, —$C(O)NR^cR^d$, or —$NR^cR^d$, each of $R^a$, $R^b$, $R^c$ and $R^d$ is independently selected from a hydrogen atom, an alkyl group, a substituted alkyl group, an alkenyl group, a substituted alkenyl group, an alkynyl group, a substituted alkynyl group, a haloalkyl group, a cycloalkyl group, a substituted cycloaklyl group, a heterocyclic group, a substituted heterocyclic group, an aryl group, a substituted aryl group, a heteroaralkyl group, or a substituted heteroaralkyl group;

or $R^c$ and $R^d$ taken together with the nitrogen to which they are attached forms a heterocyclic group, a substituted heterocyclic group, a heteroaryl group or a substituted heteroaryl group; and n is 0, 1 or 2.

2. A compound of formula (II), a salt thereof, or an enantiomer thereof, (II)

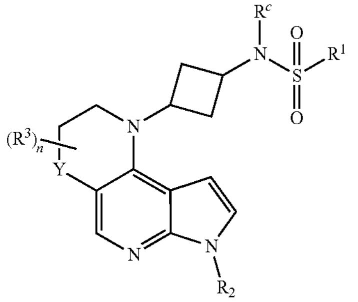

a salt thereof, or an enantiomer thereof, wherein:

Y is O, S, N or —CH;

$R^1$ is a hydrogen atom, an alkyl group, a substituted alkyl-radical group, an alkenyl group, a substituted alkenyl group, an alkynyl group, a substituted alkynyl group, an aralkyl group, a substituted aralkyl group, an alkoxy group, a substituted alkoxy group, a cyclic amine group, a heterocyclic group, a substituted heterocyclic group, a cycloalkyl group, a substituted cycloaklyl group, a heteroaralkyl group, a substituted heteroaralkyl group, a heterocyclic amine group, —$NR^cR^d$, —$NR^cC(O)R^b$, —$NR^cC(O)OR^a$, —$NR^cC(O)NR^cR^d$, —$NR^cS(O)R^b$, —$NR^cS(O)_2R^b$, —$NR^cS(O)_2NR^cR^d$, —$OC(O)R^b$, or —$OC(O)NR^cR^d$, $R^2$ is a hydrogen atom, an alkyl group or a substituted alkyl group, an alkenyl group, a substituted alkenyl group, an alkynyl group, a substituted alkynyl group, an aryl group, a substituted aryl group, a heterocyclic group, or a substituted heterocyclic group;

$R^3$ is independently selected from a hydrogen atom, an alkyl group, a substituted alkyl group, an alkenyl group, a substituted alkenyl group, an alkynyl group, a substituted alkynyl group, an alkoxy group, a haloalkyl group, a halogen, a cycloalkyl group, a substituted cycloalkyl group, —CN, —$NO_2$, —$C(O)OR^a$, —$C(O)NR^cR^d$, or —$NR^cR^d$;

each of $R^a$, $R^b$, $R^c$ and $R^d$ is independently selected from a hydrogen atom, an alkyl group, a substituted alkyl group, an alkenyl group, a substituted alkenyl group, an alkynyl group, a substituted alkynyl group, a haloalkyl, a cycloalkyl, a substituted cycloaklyl, a heterocyclic, a substituted heterocyclic group, an aryl group, a substituted aryl group, a heteroaralkyl group, or a substituted heteroaralkyl group;

or $R^c$ and $R^d$ taken together with the nitrogen to which they are attached forms a heterocyclic radical group, a substituted heterocyclic group, a heteroaryl group or a substituted heteroaryl group; and n is 0, 1, or 2.

3. The compound as claimed in claim 2, a salt thereof, or an enantiomer thereof, wherein:

Y is O;

$R^1$ is a heterocyclic group or a substituted heterocyclic group, a cycloalkyl group, a substituted cycloaklyl group, a heteroaralkyl group, a substituted heteroaralkyl group, or a heterocyclic amine group;

$R^2$ is a hydrogen atom, a lower alkyl group or a lower alkyl group substituted with a flourine atom;

$R^c$ is a hydrogen atom, an alkyl group, a substituted alkyl group; and n is 0.

4. The compound as claimed in claim 2, a salt thereof, or an enantiomer thereof, wherein $R^1$ is $NR^cR^d$, wherein one of $R^c$ and $R^d$ is a methyl group and the other is a butenyl group.

5. The compound as claimed in claim 1, a salt thereof, or an enantiomer thereof, wherein $R^2$ is a hydrogen atom, a lower alkyl group or a lower alkyl group substituted with a flourine atom.

6. The compound as claimed in claim 1, a salt thereof, or an enantiomer thereof, wherein $R^2$ is a hydrogen atom.

7. The compound as claimed in claim 1, a salt thereof, or an enantiomer thereof, wherein Y is O.

8. The compound as claimed in claim 1, a salt thereof, or an enantiomer thereof, wherein n is 0.

9. The compound as claimed in claim 2, having the formula (IIa)

(IIa)

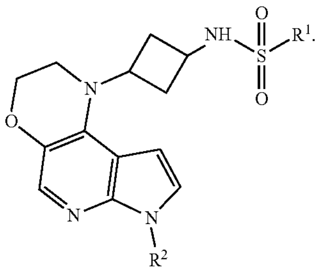

10. The compound as claimed in claim 2, a salt thereof, or an enantiomer thereof, wherein the compound is 1-Cyclopropyl-N-((cis)-3-(2,3-dihydropyrrolo[3',2':5,6]pyrido[3,4-b][1,4]oxazin-1(7H)-yl)cyclobutyl)azetidine-3-sulfonamide.

11. The compound as claimed in claim 1, having the formula:

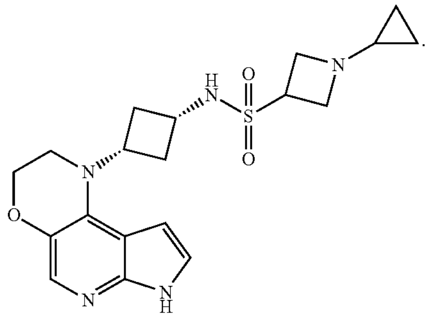

12. A composition comprising the compound as claimed in claim 1, and a pharmaceutically acceptable carrier.

* * * * *